US012232837B2

(12) United States Patent
Goswami et al.

(10) Patent No.: US 12,232,837 B2
(45) Date of Patent: *Feb. 25, 2025

(54) SYSTEMS AND METHODS FOR MASTER/TOOL REGISTRATION AND CONTROL FOR INTUITIVE MOTION

(71) Applicant: INTUITIVE SURGICAL OPERATIONS, INC., Sunnyvale, CA (US)

(72) Inventors: Ambarish G. Goswami, Fremont, CA (US); Paul G. Griffiths, Santa Clara, CA (US); Brandon D. Itkowitz, San Jose, CA (US); Tao Zhao, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/531,965

(22) Filed: Dec. 7, 2023

(65) Prior Publication Data
US 2024/0108426 A1 Apr. 4, 2024

Related U.S. Application Data

(62) Division of application No. 16/763,552, filed as application No. PCT/US2018/061729 on Nov. 19, 2018, now Pat. No. 11,877,816.
(Continued)

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/70* (2016.02); *A61B 90/37* (2016.02); *A61B 90/39* (2016.02); *A61B 2034/301* (2016.02)

(58) Field of Classification Search
CPC ......... A61B 34/35; A61B 34/37; A61B 34/70; A61B 90/37; A61B 90/39
(Continued)

(56) References Cited

U.S. PATENT DOCUMENTS 6,044,308 A 3/2000 Huissoon
6,671,581 B2 12/2003 Niemeyer et al.
(Continued)

FOREIGN PATENT DOCUMENTS

KR 101527176 B1 6/2015
WO WO-2013023130 A1 2/2013
(Continued)

OTHER PUBLICATIONS

Extended European Search Report for Application No. EP18881976.7 mailed on Dec. 21, 2020, 9 pages.
(Continued)

*Primary Examiner* — Aaron F Roane
(74) *Attorney, Agent, or Firm* — Haynes & Boone, LLP.

(57) ABSTRACT

A robotic system comprises an input device movable by an operator and a processing unit. An operator reference frame is defined relative to the operator. The processing unit is configured to present, to the operator, a first image of a first tool captured by an imaging device, receive, from the operator, a first indication that a first axis of the input device is aligned with a corresponding axis of the first tool in the first image, and in response to the first indication, determine a first alignment relationship between the imaging device and the first tool based on a second alignment relationship between the operator reference frame and the input device.

20 Claims, 16 Drawing Sheets

Related U.S. Application Data

(60) Provisional application No. 62/588,964, filed on Nov. 21, 2017.

(51) Int. Cl.
*A61B 90/00* (2016.01)
*A61B 34/30* (2016.01)

(58) Field of Classification Search
USPC .............................................................. 606/1
See application file for complete search history.

(56) References Cited

U.S. PATENT DOCUMENTS

| | | | |
|---|---|---|---|
| 6,837,883 | B2 | 1/2005 | Moll et al. |
| 7,010,390 | B2 | 3/2006 | Graf et al. |
| 8,108,072 | B2 | 1/2012 | Zhao et al. |
| 9,259,289 | B2 | 2/2016 | Zhao et al. |
| 11,877,816 | B2 | 1/2024 | Goswami et al. |
| 2005/0107920 | A1 | 5/2005 | Ban et al. |
| 2006/0258938 | A1 | 11/2006 | Hoffman et al. |
| 2010/0168763 | A1 | 7/2010 | Zhao et al. |
| 2011/0320039 | A1 | 12/2011 | Hsu et al. |
| 2014/0100694 | A1 | 4/2014 | Rueckl et al. |
| 2014/0135792 | A1 | 5/2014 | Larkin et al. |
| 2014/0275997 | A1 | 9/2014 | Chopra et al. |
| 2016/0023355 | A1 | 1/2016 | Komatsu et al. |
| 2016/0030117 | A1 | 2/2016 | Mewes |
| 2016/0206387 | A1 | 7/2016 | Zhao et al. |
| 2016/0346930 | A1 | 12/2016 | Hares |
| 2017/0000574 | A1* | 1/2017 | Itkowitz ............... A61B 1/0016 |
| 2020/0360097 | A1 | 11/2020 | Dimaio et al. |
| 2021/0369365 | A1 | 12/2021 | Goswami et al. |

FOREIGN PATENT DOCUMENTS

| | | |
|---|---|---|
| WO | WO-2015142953 A1 | 9/2015 |
| WO | WO-2016069655 A1 | 5/2016 |
| WO | WO-2016149345 A1 | 9/2016 |
| WO | WO-2016201207 A1 | 12/2016 |
| WO | WO-2017062370 A1 | 4/2017 |
| WO | WO-2019009346 A1 | 1/2019 |
| WO | WO-2019099346 A2 | 5/2019 |
| WO | WO-2019139949 A1 | 7/2019 |

OTHER PUBLICATIONS

International Preliminary Report on Patentability for Application No. PCT/US2018/061729, mailed on Jun. 4, 2020, 6 pages.
International Search Report and Written Opinion for Application No. PCT/US2018/061729, mailed on Mar. 6, 2019, 9 pages.
Office Action for Chinese Application No. CN201880035658.2, mailed Dec. 9, 2023, 17 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

SYSTEMS AND METHODS FOR MASTER/TOOL REGISTRATION AND CONTROL FOR INTUITIVE MOTION

CROSS-REFERENCE TO RELATED APPLICATIONS

This application is a divisional of U.S. patent application Ser. No. 16/763,552 filed May 12, 2020 which is the U.S. National Phase of International Patent Application No. PCT/US2018/061729, filed Nov. 19, 2018, which designated the U.S. and claims priority to and the benefit of U.S. Provisional Application No. 62/588,964, filed Nov. 21, 2017, all of which are incorporated by reference herein in their entirety.

FIELD

The present disclosure is directed to systems and methods for performing a robotic procedure, and more particularly to systems and methods for determining a master-to-tool transformation used in controlling the movement of a tool.

BACKGROUND

Robotic manipulator assemblies include robotic manipulators that can be operated to control the motion of tools in a workspace. For example, such robotic manipulators can be used to perform non-medical and medical procedures. As a specific example, teleoperated surgical manipulators can be used to perform minimally invasive medical techniques.

It is desirable in medical techniques to reduce the amount of tissue that is damaged during medical procedures, thereby reducing patient recovery time, discomfort, and harmful side effects. For example, minimally invasive techniques may be performed through natural orifices in a patient anatomy or through one or more incisions. Through these natural orifices or incisions, clinicians may insert medical tools to reach a target tissue location. Minimally invasive medical tools include tools such as therapeutic tools, diagnostic tools, and surgical tools. Minimally invasive medical tools may also include imaging tools such as endoscopic tools that provide a user with a field of view within the patient anatomy.

Robotic manipulators may be teleoperated or otherwise computer-assisted. For performing and viewing a robotic procedure at a procedure site (e.g., a surgical site within a patient), two or more slave manipulators may be used for holding and manipulating tools, including for example surgical instrument tools and imaging tools. To manipulate these tools, an operator's control console often includes master control devices which may be selectively associated with the tools and the slave manipulators holding the tools to manipulate them. In such a robotic system, the control of a tool in response to operator manipulation of a master control device may have a number of definable reference frames and corresponding frame transformations to map points in one frame to corresponding points in another frame. When one or more of the position and orientation of the frames and/or frame transformations are unknown, however, precise control of the tools may be difficult to achieve. In such cases, the success rate or accuracy of the procedure may be reduced. In a medical robot context, the safety of a patient being treated at the time by the robotic medical system as well as the successful completion of a procedure being performed on the patient may be jeopardized.

SUMMARY

The embodiments of the invention are summarized by the claims that follow below.

In one illustrative embodiment, a robotic system comprises a display that is viewable by an operator. An operator reference frame is defined relative to the display or the operator viewing the display. The robotic system further comprises an input device movable by the operator and processing unit including one or more processors. The processing unit is configured to present, in the display, a first image of a first tool captured by an imaging device. The processing unit is also configured to receive, from the operator, a first indication that a first axis of the input device is aligned with a corresponding axis of the first tool in the first image. The processing unit is also configured to in response to the first indication, determine a first alignment relationship between the imaging device and the first tool based on a second alignment relationship between the operator reference frame and the input device.

In another illustrative embodiment, a method comprises presenting, in a display that is viewable by an operator, a first image of a first tool captured by an imaging device. A first indication that a first axis of an input device movable by the operator is aligned with a corresponding axis of the first tool in the first image is received from the operator. In response to the first indication, a first alignment relationship between the imaging device and the first tool is determined based on a second alignment relationship between an operator reference frame and the input device. The operator reference frame is defined relative to the display or the operator viewing the display.

In another illustrative embodiment, a non-transitory machine-readable medium comprises a plurality of machine-readable instructions which, when executed by one or more processors, are adapted to cause the one or more processors to perform a method. The method includes presenting, in a display that is viewable by an operator, a first image of a first tool captured by an imaging device. A first indication that a first axis of an input device movable by the operator is aligned with a corresponding axis of the first tool in the first image is received from the operator. In response to the first indication, a first alignment relationship between the imaging device and the first tool is determined based on a second alignment relationship between an operator reference frame and the input device. The operator reference frame is defined relative to the display or the operator viewing the display.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples.

This repetition is for the purpose of simplicity and clarity and does not in itself dictate a relationship between the various embodiments and/or configurations discussed.

DETAILED DESCRIPTION

Figure 1A:
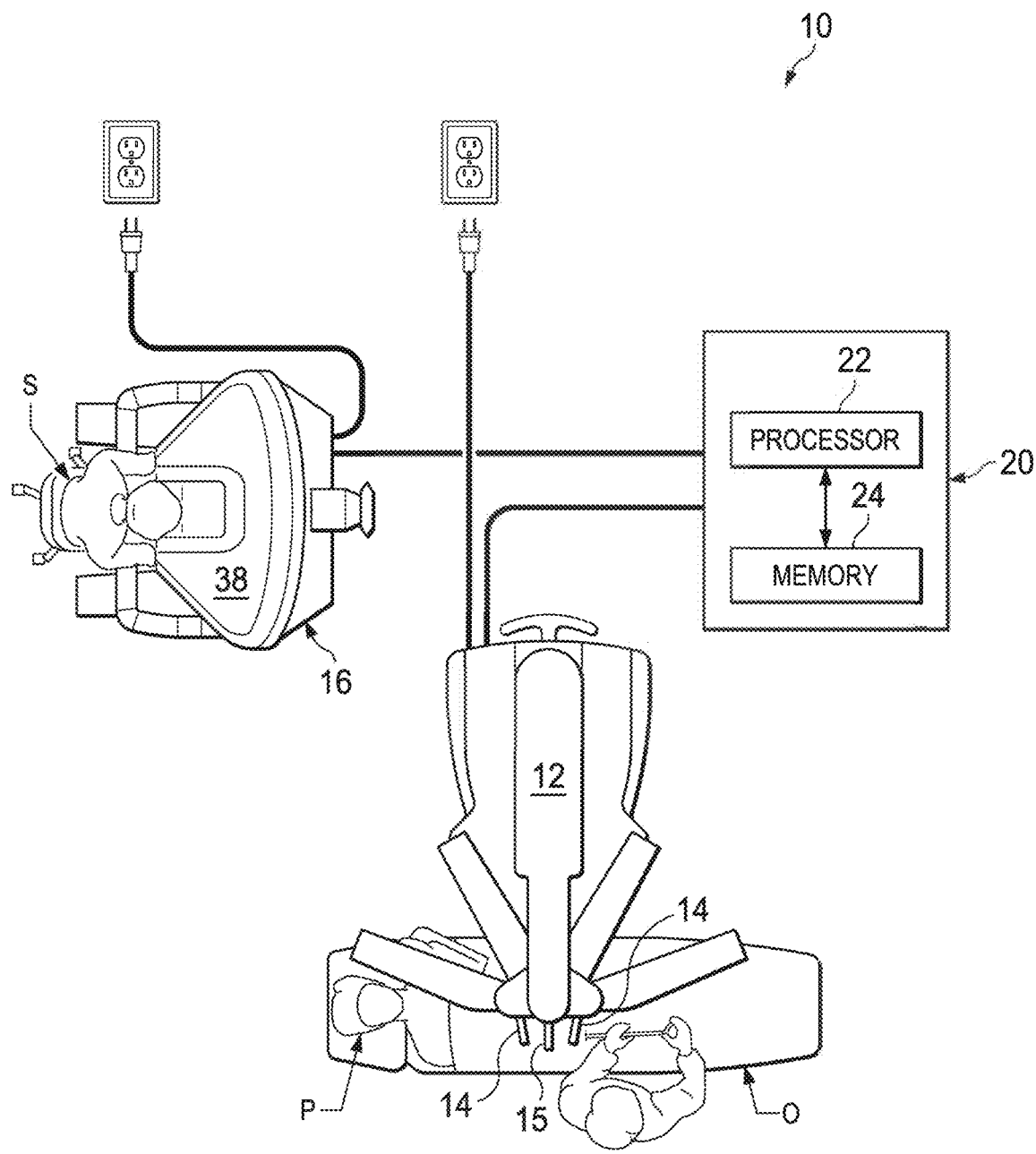
FIG. 1A is a schematic view of a robotic medical system, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances, well-known methods, procedures, components, and circuits have not been described in detail so as not to unnecessarily obscure aspects of the embodiments of the invention.

Any alterations and further modifications to the described devices, tools, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances, the same reference numbers are used throughout the drawings to refer to the same or like parts.

Although some of the examples described herein often refer to surgical procedures or tools, or medical procedures or tools, the techniques disclosed also apply to non-medical procedures and non-medical tools. For example, the tools, systems, and methods described herein may be used for non-medical purposes including industrial uses, general robotic uses, and sensing or manipulation of non-tissue work pieces. Other example applications involve surgical or non-surgical cosmetic improvements, imaging of or gathering data from human or animal anatomy, training medical or non-medical personnel, performing procedures on tissue removed from human or animal anatomies (without return to a human or animal anatomy), and performing procedures on human or animal cadavers.

The embodiments below will describe various tools and portions of tools in terms of their state in three-dimensional space. As used herein, the term "position" refers to the location of an object or a portion of an object in a three-dimensional space (e.g., three degrees of translational freedom that can be described using changes in Cartesian X, Y, Z coordinates, such as along Cartesian X, Y, Z axes). As used herein, the term "orientation" refers to the rotational placement of an object or a portion of an object (three degrees of rotational freedom—e.g., which can be described using roll, pitch, and yaw). As used herein, the term "pose" refers to the position of an object or a portion of an object in at least one degree of translational freedom, and to the orientation of that object or that portion of that object in at least one degree of rotational freedom. For an asymmetric, rigid body in a three-dimensional space, a full pose can be described with six parameters in six total degrees of freedom.

Referring to FIG. 1A of the drawings, an example robotic system is shown. Specifically, in FIG. 1A, a computer-aided, robotic medical system that may be teleoperated and used in, for example, medical procedures including diagnostic, therapeutic, or surgical procedures, is generally indicated by the reference numeral 10. As will be described, the teleoperational systems of this disclosure are under the teleoperational control of an operator. In some embodiments, manipulators or other parts of a robotic system may be controlled directly through manual interaction with the manipulators (or the other parts) themselves. Thus, "teleoperated manipulators" as used in this application include manipulators that can be controlled only through teleoperation, and manipulators that can be controlled through teleoperation and through direct manual control. Further, in some embodiments, a non-teleoperational or robotic medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures.

As shown in FIG. 1A, the robotic medical system 10 generally includes a manipulator assembly 12 mounted to or near an operating table O on which a patient P is positioned. The manipulator assemblies described herein often include one or more robotic manipulators and tools mounted thereon, although the term "manipulator assembly" also encompasses the manipulator without the tool mounted thereon. The manipulator assembly 12 may be referred to as a patient side cart in this example, since it comprises a cart and is designed to be used next to a patient. A medical tool 14 (also referred to as a tool 14) and a medical tool 15 are operably coupled to the manipulator assembly 12. Within this disclosure, the medical tool 15 includes an imaging device, and may also be referred to as the imaging tool 15. The imaging tool 15 may comprise an endoscopic imaging system using optical imaging technology, or comprise another type of imaging system using other technology (e.g. ultrasonic, fluoroscopic, etc.). An operator input system 16 allows an operator such as a surgeon or other type of clinician S to view images of or representing the procedure site and to control the operation of the medical tool 14 and/or the imaging tool 15.

The operator input system 16 for the robotic medical system 10 may be "mechanically grounded" by being connected to a base with linkages such as to an operator's console, or it may be "mechanically ungrounded" and not be thus connected. As shown in FIG. 1A, the operator input system 16 is connected to an operator's console 38 that is usually located in the same room as operating table O during a surgical procedure. It should be understood, however, that the operator S can be located in a different room or a completely different building from the patient P. The operator input system 16 generally includes one or more control device(s) for controlling the medical tool 14. The operator input system 16 is also referred to herein as "master manipulators," "master control devices," "master input devices," and "input devices." The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and the like. In some embodiments, the control device(s) will be provided with the same degrees of freedom as the medical tools of the robotic assembly to provide the operator with telepresence; that is, the operator is provided with the perception that the control device(s) are integral with the tools so that the operator has a sense of directly controlling tools as if present at the procedure site. In other embodiments, the control device(s) may have more or fewer degrees of freedom than the associated medical tools and still provide the operator with telepresence. In some embodiments, the control device(s) are manual input devices which move with six degrees of freedom, and which may also include an actuatable handle for actuating medical tools (for example, for closing grasping jaw end effectors, applying an electrical potential to an electrode, capture images, delivering a medicinal treatment, and the like).

The manipulator assembly 12 supports and manipulates the medical tool 14 while the operator S views the procedure site through the operator's console. An image of the procedure site can be obtained by the medical tool 15, such as via an imaging system comprising a monoscopic or stereoscopic endoscope, which can be manipulated by the manipulator assembly 12 to orient the medical tool 15. An electronics cart can be used to process the images of the procedure site for subsequent display to the operator S through the operator's console. The number of medical tools 14 used at one time will generally depend on the medical diagnostic or treatment (e.g. surgical) procedure and the space constraints within the operating room among other factors. The manipulator assembly 12 may include a kinematic structure of one or more non-servo controlled links (e.g., one or more links that may be manually positioned and locked in place) and a robotic manipulator. The manipulator assembly 12 includes a plurality of motors that drive inputs on the medical tools 14. These motors move in response to commands from the control system (e.g., control system 20). The motors include drive systems which when coupled to the medical tools 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the tool for grasping tissue in the jaws of a biopsy device or the like. The medical tools 14 may include end effectors having a single working member such as a scalpel, a blunt blade, a needle, an imaging sensor, an optical fiber, an electrode, etc. Other end effectors may include multiple working members, and examples include forceps, graspers, scissors, clip appliers, staplers, bipolar electrocautery instruments, etc.

The robotic medical system 10 also includes a control system 20. The control system 20 includes at least one memory 24 and at least one processor 22, and typically a plurality of processors, for effecting control between the medical tool 14, the operator input system 16, and other auxiliary systems 26 which may include, for example, imaging systems, audio systems, fluid delivery systems, display systems, illumination systems, steering control systems, irrigation systems, and/or suction systems. The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the manipulator assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 20 supports wireless communication protocols such as Bluetooth, IrDA, HomeRF, IEEE 802.11, DECT, and Wireless Telemetry.

In some embodiments, the control system 20 may include one or more servo controllers that receive force and/or torque feedback from the medical tool 14 or from the manipulator assembly 12. Responsive to the feedback, the servo controllers transmit signals to the operator input system 16. The servo controller(s) may also transmit signals that instruct the manipulator assembly 12 to move the medical tool(s) 14 and/or 15 which extends into an internal procedure site within the patient body via openings in the body. Any suitable conventional or specialized controller may be used. A controller may be separate from, or integrated with, manipulator assembly 12. In some embodiments, the controller and manipulator assembly are provided as part of an integrated system such as a teleoperational arm cart positioned proximate to the patient's body during the medical procedure.

The control system 20 can be coupled to the medical tool 15 and can include a processor to process captured images for subsequent display, such as to an operator using the operator's console or wearing a head-mounted display system, on one or more stationary or movable monitors near the control system, or on another suitable display located locally and/or remotely. For example, where a stereoscopic endoscope is used, the control system 20 can process the captured images to present the operator with coordinated stereo images of the procedure site. Such coordination can include alignment between the stereo images and can include adjusting the stereo working distance of the stereoscopic endoscope.

In alternative embodiments, the robotic system may include more than one manipulator assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

Figure 1B:
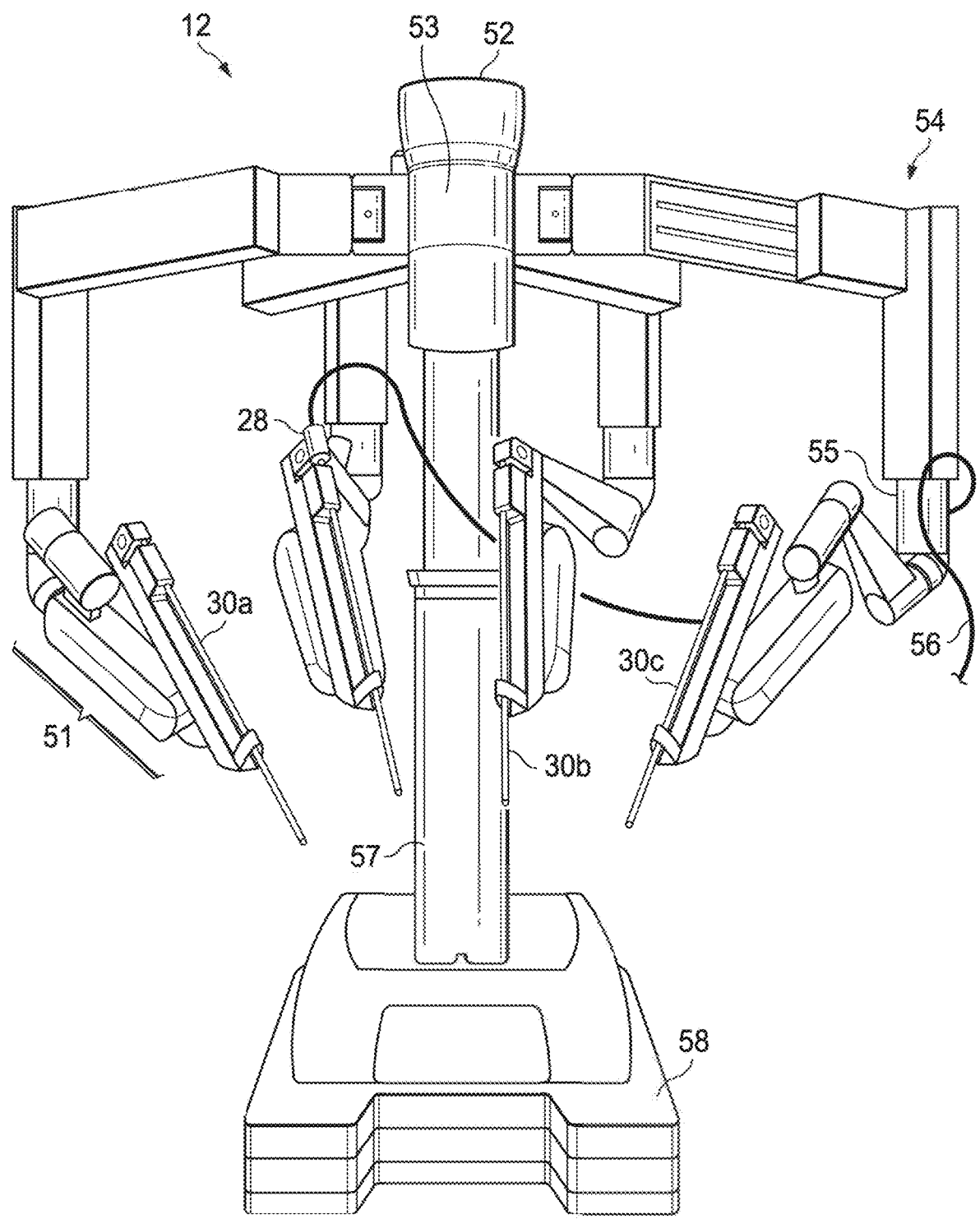
FIG. 1B is a perspective view of a manipulator assembly, in accordance with an embodiment of the present disclosure.

FIG. 1B is a perspective view of one embodiment of a manipulator assembly 12 that is configured in the form of a cart that is located near the patient during a medical procedure. Thus, this manipulator assembly of FIG. 1B may also be referred to as a patient side cart. The manipulator assembly 12 shown provides for the manipulation of three medical tools 30a, 30b, 30c (e.g., medical tools 14) and a medical tool 28 including an imaging device (e.g., medical tool 15), such as a stereoscopic endoscope used for the capture of images of the workpiece or of the site of the procedure (also called "work site"). The medical tool 28 may transmit signals over a cable 56 to the control system 20. Manipulation is provided by robotic manipulators having a number of joints. The medical tool 28 and the surgical tools 30a-c can be positioned and manipulated through incisions in, or natural orifices of, the patient so that a kinematic remote center is maintained at the incisions or natural orifices. Images of the work site can include images of the distal ends of the surgical tools 30a-c when they are positioned within the field-of-view of the imaging device of the medical tool 28.

The manipulator assembly 12 includes a movable, lockable, and drivable base 58. The base 58 is connected to a telescoping column 57, which allows for adjustment of the height of the arms 54 (also called "manipulators 54"). The arms 54 may include a rotating joint 55 that both rotates and translates parallel to the column 57. The arms 54 may be connected to an orienting platform 53. The orienting platform 53 may be capable of 360 degrees of rotation. The manipulator assembly 12 may also include a telescoping horizontal cantilever 52 for moving the orienting platform 53 in a horizontal direction.

In the present example, each of the arms 54 includes a manipulator arm portion 51. The manipulator arm portion 51 may connect directly to a medical tool 14. The manipulator arm portion 51 may be teleoperatable. In some examples, the arms 54 connecting to the orienting platform are not teleoperatable. Rather, such arms 54 are positioned as desired before the operator S begins operation with the teleoperative components.

Endoscopic and other imaging systems (e.g., medical tool 15) may be provided in a variety of configurations, including ones having rigid or flexible structures. Rigid endoscopes include a rigid tube housing a relay lens system for transmitting an image from a distal end to a proximal end of the endoscope. Flexible endoscopes transmit images using one or more flexible optical fibers. Digital image based endoscopes may have a "chip on the tip" design in which a distal digital sensor such as a one or more charge-coupled device (CCD) or a complementary metal oxide semiconductor (CMOS) device store image data. Endoscopic imaging systems may also utilize other imaging techniques such as ultrasonic, infrared, and fluoroscopic technologies. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic tools employ stereo cameras to capture stereo images of the patient anatomy. An endoscopic tool may be a fully sterilizable assembly with the endoscope cable, handle and shaft all rigidly coupled and hermetically sealed.

Figure 1C:
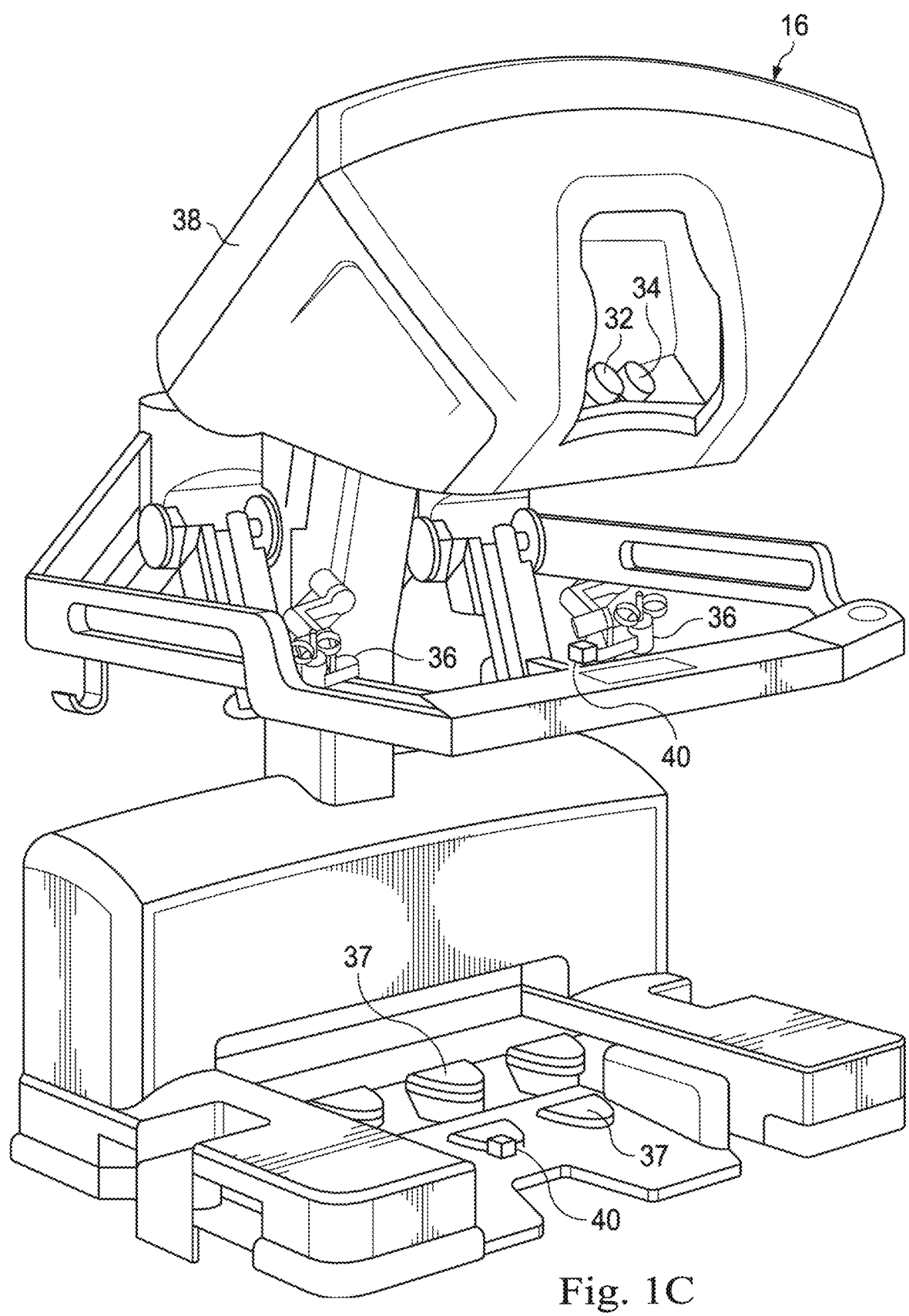
FIG. 1C is a perspective view of an operator's control console for a robotic medical system, in accordance with an embodiment of the present disclosure.

FIG. 1C is a perspective view of the operator's console 38. The operator's console 38 includes a left eye display 32 and a right eye display 34 for presenting the operator S with a coordinated stereo view of the surgical environment that enables depth perception. An operator input system 16 of the operator's console 38 includes one or more input control devices 36, which in turn causes the manipulator assembly 12 to manipulate one or more medical tools 14 and/or 15. The input control devices 36 may be used to, for example, close grasping jaw end effectors, apply an electrical potential to an electrode, deliver a medicinal treatment, or the like. In various alternatives, the input control devices 36 may additionally or alternatively include joystick devices, trackballs, data gloves, trigger-guns, hand-operated controllers, voice recognition devices, touch screens, body motion or presence sensors, and the like. In some embodiments and for some associated medical tools 14, the input control devices 36 will provide the same degrees of freedom as their associated medical tools 14 to provide the operator S with telepresence, or the perception that the input control devices 36 are integral with the tools 14 so that the operator S has a sense of directly controlling the tools 14. In other embodiments, the input control devices 36 may have more or fewer degrees of freedom than the associated medical tools and still provide the operator S with telepresence. To this end, position, force, and tactile feedback sensors may be employed to transmit position, force, and tactile sensations from the tools 14 back to the operator S's hands through the input control devices 36. An operator input system 16 of the operator's console 38 may also include input control devices 37, which are foot pedals that receive input from a user's foot.

Figure 2:
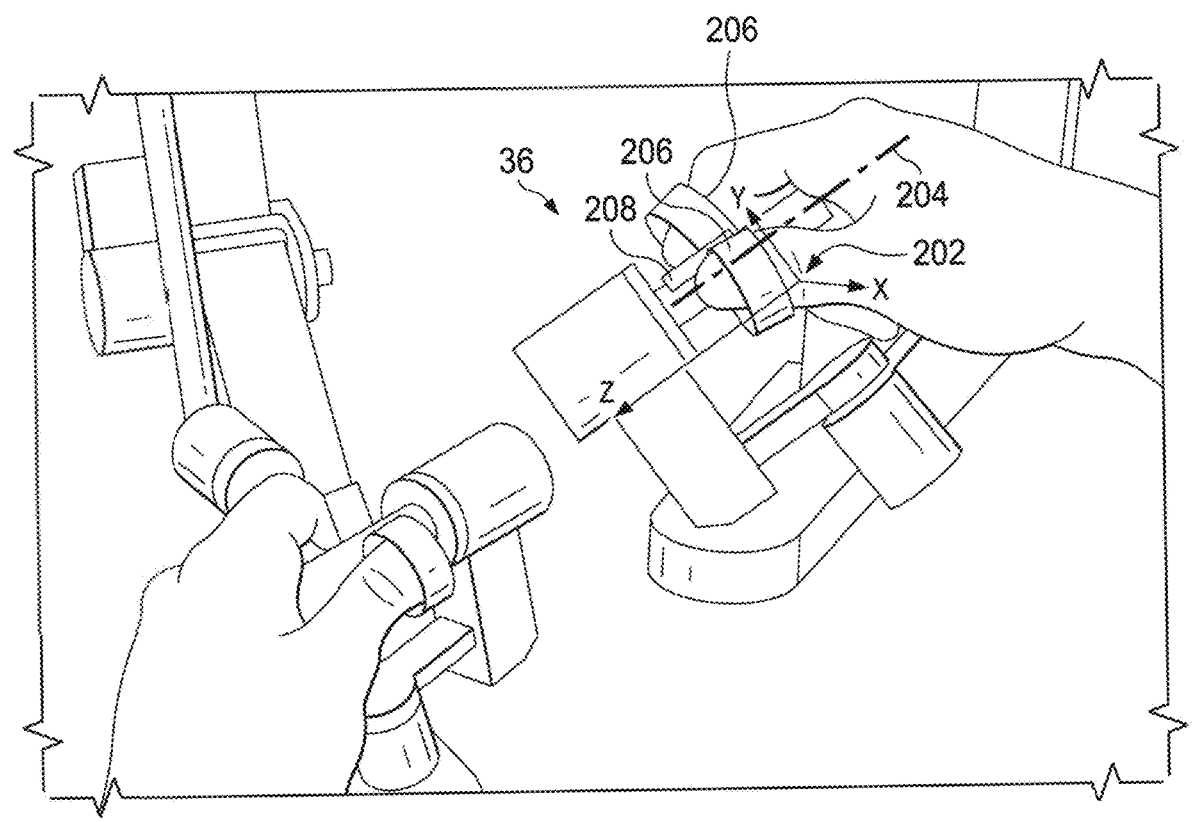
FIG. 2 is a perspective view of an operator's input controller, in accordance with an embodiment of the present disclosure.

As shown in FIG. 2, in some embodiments, input control devices 36 may include one or more of any number of a variety of input devices such as grip inputs 206 and trigger switches 208. As illustrated in the example of FIG. 2, a master reference frame 202 associated with the input control device 36, denoted as m1, is provided. The Z-axis of the master reference frame 202 is parallel to an axis of symmetry 204 of the input control device 36. The X and Y axes of the master reference frame 202 extend perpendicularly from the axis of symmetry 204.

Figure 3A:
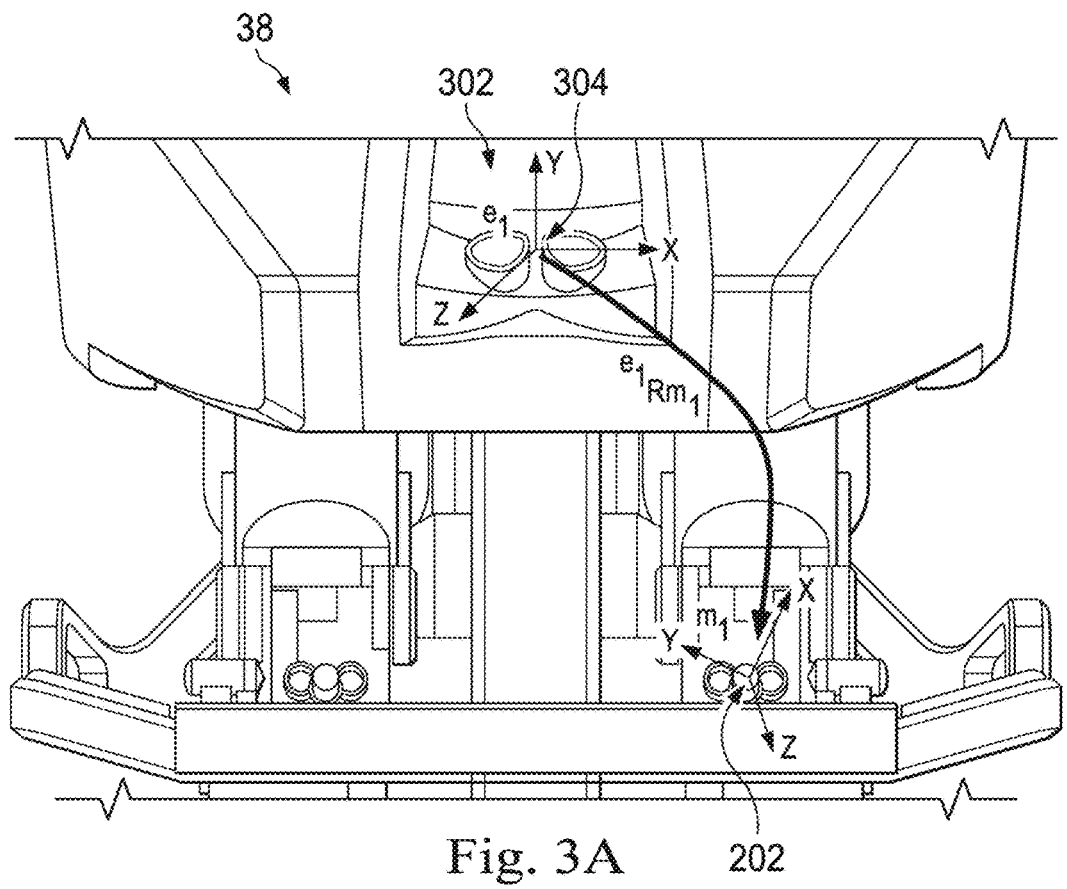
FIG. 3A is a perspective view of an operator's control console for a robotic medical system, in accordance with an embodiment of the present disclosure.
Figure 3B:
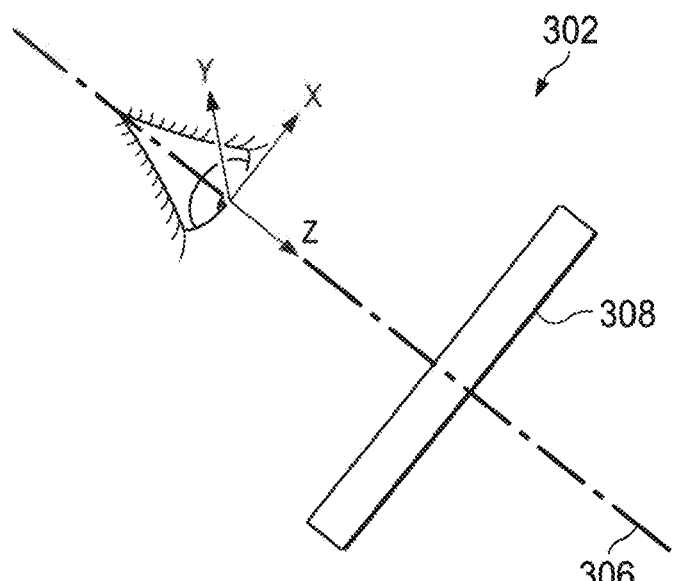
FIG. 3B is a schematic view illustrating an operator reference frame associated with an operator of the robotic medical system relative to a display of an operator's control console, in accordance with an embodiment of the present disclosure.

Referring to FIGS. 3A and 3B, these figures show an operator reference frame 302, denoted as e1. In various embodiments, the operator reference frame 302 may correspond with any appropriate portion of the operating environment, or with the operating environment itself. For example, the origin, the orientation, or both origin and orientation of the operator reference frame 302 may correspond with a part of the operator S, or a part of the robotic system. As specific examples, the operator reference frame 302 may have an origin based on the position of, and an orientation based on the orientation of, part or all of, the operator S (including, for example, the head, the torso, the entire body, or another body part of the operator). As further examples, the operator reference frame 302 may be based on a position of something held or otherwise attached to the operator, such as a head-mounted display, one or more hand-held input device, tracking markers or sensors attached to the operator S, etc. As yet further examples, the operator reference frame 302 may coincide with a display screen used to display images of the work space, a sensor system used to detect the operator S (or items attached to the operator S). Such a sensor system may be placed near the operator S or the display screen, such as on top of, below, or next to the operator or display screen. In an embodiment, the operator reference frame 302 corresponds to a location and orientation of a viewer of the system through which the operator looks through to the work site.

In the examples of the FIGS. 3A and 3B, the operator reference frame 302 is defined with both origin and orientation corresponding with the usual or expected position and orientation the operator S's eyes, when the operator S is viewing the surgical site on a display 308 of an operator's console 38. As such, this operator reference frame 302 is sometimes referred to as an eye reference frame. In the FIGS. 3A and 3B example, the Z-axis of the operator reference frame 302 extends along a line of sight 306 of the operator S, when viewing the surgical site through the display 308. The X and Y axes of the operator reference frame 302 extend perpendicularly from the Z-axis at an origin 304 of the operator reference frame 302. Forward or inverse kinematic calculations are used to transform between the master reference frame 202 m1 and the operator reference frame 302 e1. A transformation from the operator reference frame 302 to master reference frame 202 m1 is denoted as $^{e1}R_{m1}$.

Figure 4:
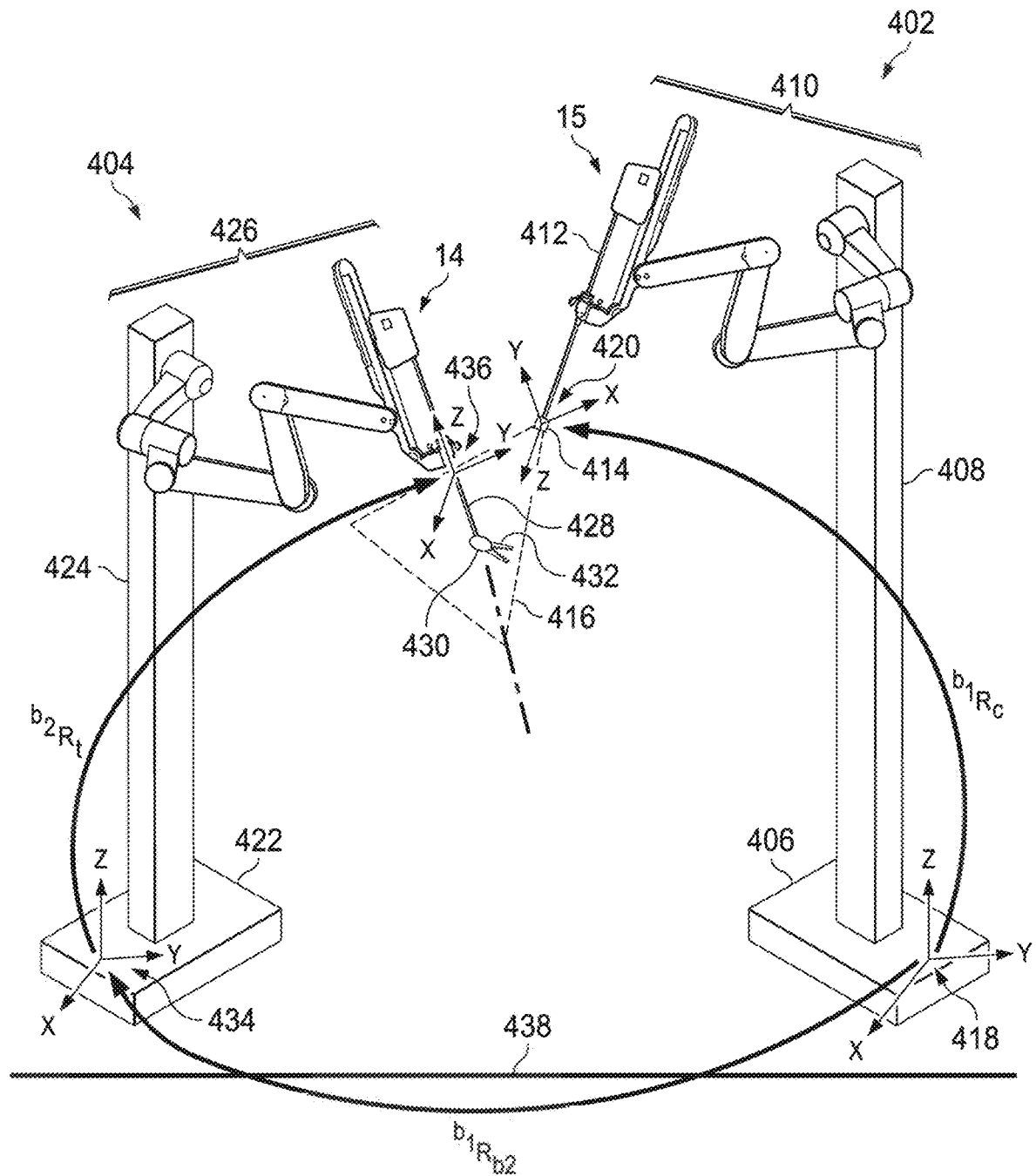
FIG. 4 is a perspective view of two manipulator assemblies of a robotic medical system, in accordance with an embodiment of the present disclosure.

Referring to the example of FIG. 4, illustrated is a robotic system (e.g., a robotic medical system 10 of FIG. 1A) including two manipulator assemblies 402 and 404 on separate bases 406 and 422 respectively. The manipulator assembly 402 includes a base 406, a structure support 408, and a manipulator 410. In the example of FIG. 4, an imaging tool 15 is mounted on the manipulator 410 and thus the manipulator assembly 402 can be considered to further include the mounted imaging tool 15. The imaging tool 15 includes a shaft 412 and an imaging device 414. The imaging device 414 may include for example an optical imager, an ultrasonic imager, an electromagnetic imager such as a fluoroscopic imager, a thermal imager, a thermoacoustic imager, and any other suitable imagers. The imaging device 414 has a field of view 416.

As illustrated in FIG. 4, the base 406 has a reference frame 418, which is also referred to as a camera base reference frame 418 and denoted as b1. The imaging device 414 has a reference frame 420, which is also referred to as a camera reference frame 420 and denoted as c. A transformation from the base reference frame 418 to the camera reference frame 420 is denoted as $^{b1}R_c$, which may be determined based on the forward kinematics of the manipulator assembly 402.

As illustrated in FIG. 4, the robotic system also includes a manipulator assembly 404. The manipulator assembly 404 includes a base 422 that is physically separate and independent from the base 406 of the manipulator assembly 402. The manipulator assembly 404 includes a structural support 424 and a manipulator 426. In the example of FIG. 4, a tool 14 is mounted on the manipulator 426, and thus the manipulator assembly 404 can be considered to further include the mounted tool 14. The tool 14 includes a shaft 428, a wrist 430 coupled to the distal end of the shaft 428, and an end effector 432 coupled to the wrist 430. The base 422 has a reference frame 434, which is also referred to as a tool base reference frame 434 and denoted as b2. The shaft 428 of the tool 14 has a reference frame 436, which is also referred to as a shaft reference frame 436 and denoted as s. A transformation from the tool base reference frame 434 to the shaft reference frame 436 is denoted as $^{b2}R_s$. The transformation $^{b2}R_s$ may be determined based on the forward kinematics of the manipulator assembly 404.

In various embodiments, the relative positions and orientations of the bases 406 and 422 are unknown. As such, the transformation $^{b1}R_{b2}$ from the camera base reference frame 418 b1 to the tool base reference frame 434 b2 is unknown. In some embodiments, as illustrated in FIG. 4, the bases 406 and 422 are coplanar or on parallel planes, such as located on a horizontal and even surface (herein called plane 438). In those embodiments, a transformation $^{b1}R_{b2}$ from a camera base reference frame 418 to a tool base reference frame 434 may be described using a single rotational parameter representing a rotation around the Z-axis perpendicular to the plane (e.g., plane 438) since the camera and tool bases reference frames 418, 434 are not rotated relative to each other along the X and Y axes defining the plane (e.g., plane 438). Alternatively, in some embodiments, the bases 406 and 422 are not coplanar, such as located on a ground that is not even. In those embodiments, the transformation $^{b1}R_{b2}$ may be described using multiple rotational parameters representing rotations around the X, Y, and/or Z-axes.

Such an unknown alignment relationship between the bases 406 and 422 may make intuitive control of a slave tool/end effector by a master control device difficult. To provide an effective control relationship between a master control device and its slave tool/end effector (also referred to as a master-tool alignment), a spatial alignment between the master control device and the tool/end effector is needed. Such a spatial alignment provides a reasonably accurate relationship between the operator's perceived motion of the master control device (e.g., a proprioceptive sense) and the operator's perceived resulting motion of the tool including the shaft and the end effector (e.g., a visual sense). For example, if the operator moves a hand grasping a master control device to the left, the operator expects to perceive the associated slave tool/end effector to move to the left also. If the perceived spatial motions match, then the operator can easily control the slave's movement by moving the master control device. But if the perceived spatial motions do not match (e.g., a master control device movement to the left results in a slave movement up and to the right), then it is difficult for the operator to control the slave's movement by moving the master control device. As described in detail below, an operator-guided registration process may be used to determine the unknown alignment relationship (e.g., $^{b1}R_{b2}$) between the bases 406 and 422, which may then be used to determine the master-tool alignment and a master-tool transformation. The operator-guided registration process may determine the master-tool alignment using registration information provided by the operator-guided registration process and known kinematic relationships and reference frame transforms in the telesurgical system. These relationships are described below in Cartesian terms, although other 3-dimensional coordinate systems may be used.

During an operator-guided registration process, an operator S may move a master control device to align the master control device (e.g., input control device 36) with an alignment target of the manipulator assembly 404. The alignment target may be a manipulator 426, a shaft 428, a wrist 430, a part or the entire end effector 432, another portion of the manipulator assembly 404, and/or a combination thereof. In an example, a portion (e.g., shaft 428, end effector 432) of the tool 14 may be used as the alignment target in the operator-guided registration process to increase the accuracy for a transformation between the camera reference frame 420 and an end effector reference frame associated with the end effector 432.

After determining the alignment target of the manipulator assembly 404, a transformation $^{c}R_{target}$ from the camera reference frame 420 (denoted as c) to an alignment target reference frame (denoted as target) associated with the alignment target satisfies the following equation:

$$^{c}R_{target} = {}^{c}R_{b1} * {}^{b1}R_{b2} * {}^{b2}R_{target}, \tag{1}$$

where $^{c}R_{b1}$ and $^{b2}R_{target}$ are known transformations that may be determined based on the forward and inverse kinematics of the manipulator assemblies 402 and 404 respectively.

When a master control device is aligned with an alignment target of the manipulator assembly 404 shown in a display of the operator's control console (e.g., a display 308 of an operator's console 38 of FIGS. 3A and 3B), the following condition of equality is satisfied:

$$^{c}R_{target} = {}^{e1}R_{m1}, \tag{2}$$

Based on equations (1) and (2), we have the following:

$$^{e1}R_{m1} = {}^{c}R_{b1} * {}^{b1}R_{b2} * {}^{b2}R_{target}. \tag{3}$$

As such, the unknown base transformation $^{b1}R_{b2}$ may be determined according to equation (3) because transformations $^{e1}R_{m1}$, $^{c}R_{b1}$, and $^{b2}R_{target}$ are all known. For example, transformation $^{e1}R_{m1}$ from the eye reference frame 302 to the master reference frame 202 may be determined based on forward kinematics of the master control device.

For further example, transformation $^{c}R_{b1}$ may be determined according to $^{c}R_{b1} = ({}^{b1}R_{c})^{-1}$, where $^{b1}R_{c}$ is a transformation from the base 406 to the imaging device 414, and may be determined using forward kinematics of the manipulator assembly 402. In the manipulator assembly 402, since the physical dimensions of all mechanical links of the manipulator assembly 402 including the imaging tool 15 are known, and since all joint angles between these mechanical links can be determined (using direct rotation sensors, motor position sensor, sensors, and the like), the kinematic relationship between the camera base reference frame 418 and camera reference frame 420 (or a reference frame of any other link in the manipulator assembly 402) may be determined using known kinematic calculations.

Likewise, transformation $^{b2}R_{target}$ may be determined using forward kinematics of the manipulator assembly 404. In the manipulator assembly 404, since the physical dimensions of all mechanical links of the manipulator assembly 404 including the tool 14 are known, and since all joint angles between these mechanical links can be determined (using direct rotation sensors, motor position sensor, sensors, and the like), the kinematic relationship between the tool base reference frame 434 and a target reference frame (e.g., a shaft reference frame 436 or a reference frame of any other portion in the manipulator assembly 404) can be determined using known kinematic calculations.

In some embodiments, the base transformation $^{b1}R_{b2}$ may be described using six parameters in six degrees of freedom, including three rotational parameters (e.g., a yaw (bearing) angle α representing a rotation around the Z-axis, a pitch angle β representing a rotation around the Y-axis, and a roll angle γ representing a rotation around the X-axis) and three translational parameters (e.g., distances x, y, and z along the X, Y, and Z-axes respectively). The transformation $^{b1}R_{b2}$ may be provided as follows:

$$^{b1}R_{b2} = [R(x,\gamma)][R(\gamma,\beta)][R(z,\alpha)]. \tag{4}$$

After the master control device is aligned with the alignment target in the display by the operator S, we have the following equation based on equations (3) and (4):

$$^{e1}R_{m1} = {}^{c}R_{b1} * [R(x,\gamma)][R(\gamma,\beta)][R(z,\alpha)] * {}^{b2}R_{target}. \tag{5}$$

Rotational and/or translational parameters between the camera base reference frame 418 and the tool base reference frame 434 may be computed based on equation (5). The transformations $^{e1}R_{m1}$, $^{c}R_{b1}$, and $^{b2}R_{target}$ may include rotational matrices describing the position and orientation relationships of two reference frames and/or transformation matrices (e.g., a homogeneous transformation matrix H) that describe both the position and orientation relationships of two reference frames.

In some embodiments, relative orientations of the camera base reference frame 418 and the tool base reference frame 434 without knowledge of relative positions of these reference frames may be sufficient to enable intuitively correct tool operations controlled by an operator using a master control device. That is, even without information about the relative positions of the camera base reference frame 418 and the tool base reference frame 434, translations and rotations at the master control device may result in corresponding translations and rotations that feel intuitively correct at the tool 14 because the relative orientations are consistent with a first alignment relationship (e.g., $^{e1}R_{m1}$) between the eye reference frame 302 and master reference frame 202 and a second alignment relationship (e.g., $^{c}R_{end\ effector}$) between the camera reference frame 420 and an end effector reference frame associated with the end effector 432. As such, in those embodiments, the operator-guided registration process may determine a transformation $^{b1}R_{b2}$ involving only rotational parameters $\alpha$, $\beta$, and $\gamma$ (without any translational parameters) for master-tool control with intuitively correct tool operations.

In some embodiments, as shown in the example of FIG. 4, the camera base 406 and the tool base 422 are on a horizontal and even plane 438. As such, the rotational parameters $\beta$ and $\gamma$ are zero. In those embodiments, the operator-guided registration process may determine a transformation $^{b1}R_{b2}$ involving only a rotational parameter $\alpha$ (without any translational parameters or rotational parameters $\beta$, and $\gamma$) for master-tool control with intuitively correct tool operations. In those embodiments, the transformation $^{b1}R_{b2}$ may be described as a Z-axis rotation having a yaw angle $\alpha$ (also referred to as a bearing angle $\alpha$) between the base frames b1 and b2. The transformation $^{b1}R_{b2}$ may be determined using a single rotational parameter (the bearing angle $\alpha$) according to equation (4) as follows:

$$^{b1}R_{b2} = [R(z, \alpha)] = \begin{bmatrix} \cos(\alpha) & -\sin(\alpha) & 0 \\ \sin(\alpha) & \cos(\alpha) & 0 \\ 0 & 0 & 1 \end{bmatrix}. \quad (6)$$

In an example where the control system determines (e.g., based on forward and inverse kinematics) that $$^{e1}R_{m1} = \begin{bmatrix} - & - & P \\ - & - & Q \\ - & - & R \end{bmatrix}, \ ^{c}R_{b1} = \begin{bmatrix} a & b & c \\ d & e & f \\ g & h & i \end{bmatrix}, \text{ and } ^{b2}R_{target} = \begin{bmatrix} j & k & l \\ m & n & p \\ q & r & s \end{bmatrix},$$

equation (3) for Z-axis transformation may be rewritten with equation (6) as follows:

$$\begin{bmatrix} - & - & P \\ - & - & Q \\ - & - & R \end{bmatrix} = \begin{bmatrix} a & b & c \\ d & e & f \\ g & h & i \end{bmatrix} \times \begin{bmatrix} \cos(\alpha) & -\sin(\alpha) & 0 \\ \sin(\alpha) & \cos(\alpha) & 0 \\ 0 & 0 & 1 \end{bmatrix} \times \begin{bmatrix} j & k & l \\ m & n & p \\ q & r & s \end{bmatrix}_z$$

$$= \begin{bmatrix} a\cos(\alpha) + b\sin(\alpha) & -a\sin(\alpha) + b\cos(\alpha) & c \\ d\cos(\alpha) + e\sin(\alpha) & -d\sin(\alpha) + e\cos(\alpha) & f \\ g\cos(\alpha) + h\sin(\alpha) & -g\sin(\alpha) + h\cos(\alpha) & i \end{bmatrix} \times \begin{bmatrix} j & k & l \\ m & n & p \\ q & r & s \end{bmatrix}_z$$

-continued $$\begin{bmatrix} P \\ Q \\ R \end{bmatrix} = \begin{bmatrix} l(a\cos(\alpha) + b\sin(\alpha)) + p(-a\sin(\alpha) + b\cos(\alpha)) + cs \\ l(d\cos(\alpha) + e\sin(\alpha)) + p(-d\sin(\alpha) + e\cos(\alpha)) + fs \\ l(g\cos(\alpha) + h\sin(\alpha)) + p(-g\sin(\alpha) + h\cos(\alpha)) + is \end{bmatrix}$$

Accordingly, three equations in one unknown parameter (the bearing angle $\alpha$) are obtained as follows:

$$(bl-ap)\sin(\alpha)+(al+bp)\cos(\alpha)=P-cs \quad (7)$$

$$(el-dp)\sin(\alpha)+(dl+ep)\cos(\alpha)=Q-fs \quad (8)$$

$$(hl-gp)\sin(\alpha)+(gl+hp)\cos(\alpha)=R-is \quad (9)$$

In some embodiments, sin(a) and cos(a) are computed using any two of the three equations (7), (8), and (9) (e.g., equations (7) and (8), equations (8) and (9), or equations (7) and (9)). For example, cos(a) may be computed using equations (7) and (8) as follows:

$$\cos(\alpha) = \frac{(Q - fs)(bl - ap) - (P - cs)(el - dp)}{(dl + ep)(bl - ap) - (al + bp)(el - dp)}. \quad (10)$$

Similarly, sin(a) may be computed using equations (7) and (8) as follows:

$$\sin(\alpha) = \frac{(Q - fs)(al + bp) - (P - cs)(dl + ep)}{(el - dp)(al + bp) - (bl - ap)(dl + ep)}. \quad (11)$$

Based on equations (10) and (11), the bearing angle $\alpha$ may be determined using an inverse tangent function based on sin(a) and cos(a). To compute sin(a) and cos(a) based on equations (10) and (11), the denominators of those equations may not be zero. In other words, in some embodiments where denominators of equations (10) and (11) are equal to zero, the bearing angle $\alpha$ may not be computed.

In some embodiments, sin(a) and cos(a) may be computed using three equations (7), (8), and (9). For example, equations (7), (8), and (9) may be rewritten as follows:

$$\begin{bmatrix} (bl - ap) & (al + bp) \\ (el - dp) & (dl + ep) \\ (hl - gp) & (gl + hp) \end{bmatrix} \times \begin{bmatrix} \sin(\alpha) \\ \cos(\alpha) \end{bmatrix} = \begin{bmatrix} P - cs \\ Q - fs \\ R - is \end{bmatrix} \quad (12)$$

A Singular Value Decomposition (SVD) algorithm may be applied to the left-hand side of the equation (12) for determining sin(a) and cos(a). The bearing angle $\alpha$ may then be determined using an inverse tangent function based on sin(a) and cos(a).

Figure 15:
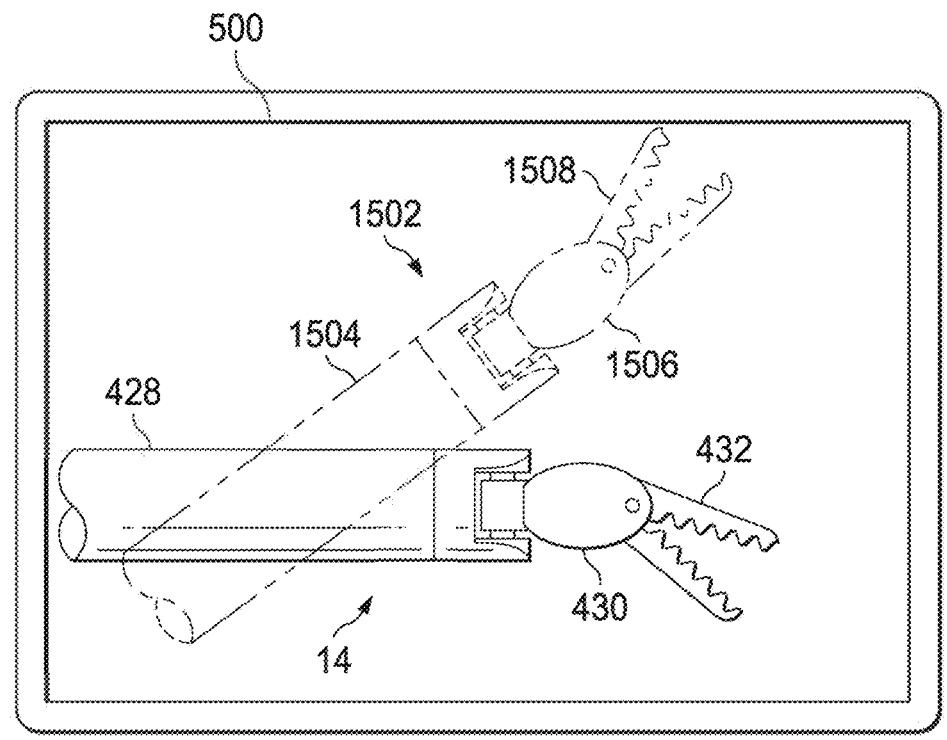
FIG. 15 illustrates an imaging view through a display of an operator's console before an operator performs an alignment step, in accordance with an embodiment of the present disclosure.
Figure 16:
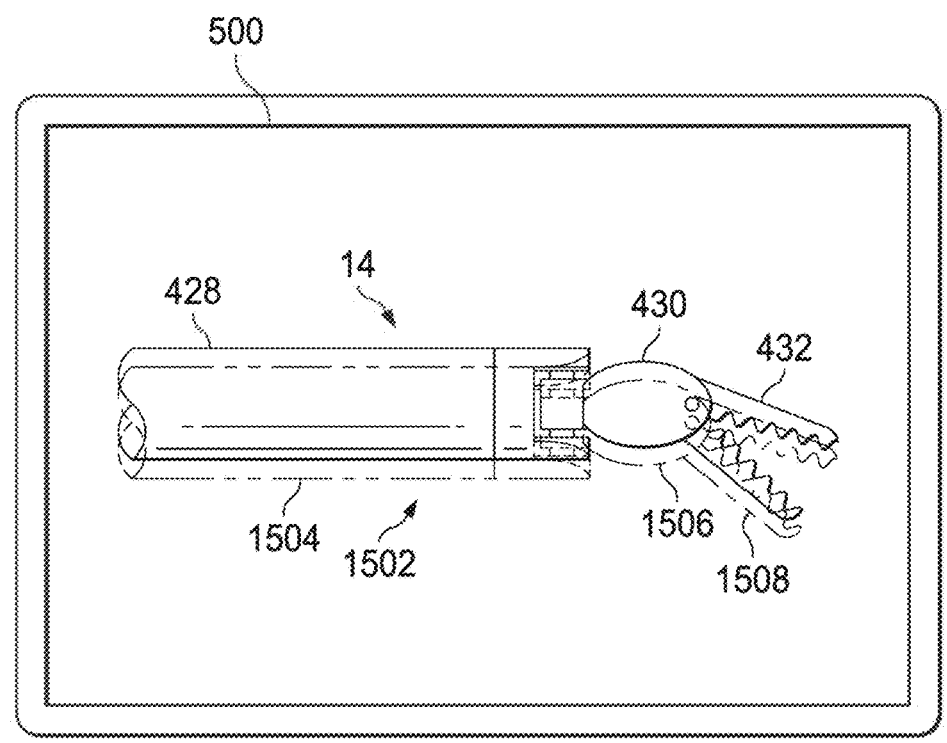
FIG. 16 illustrates an imaging view through a display of an operator's console after an operator performs an alignment step, in accordance with an embodiment of the present disclosure.
Figure 17:
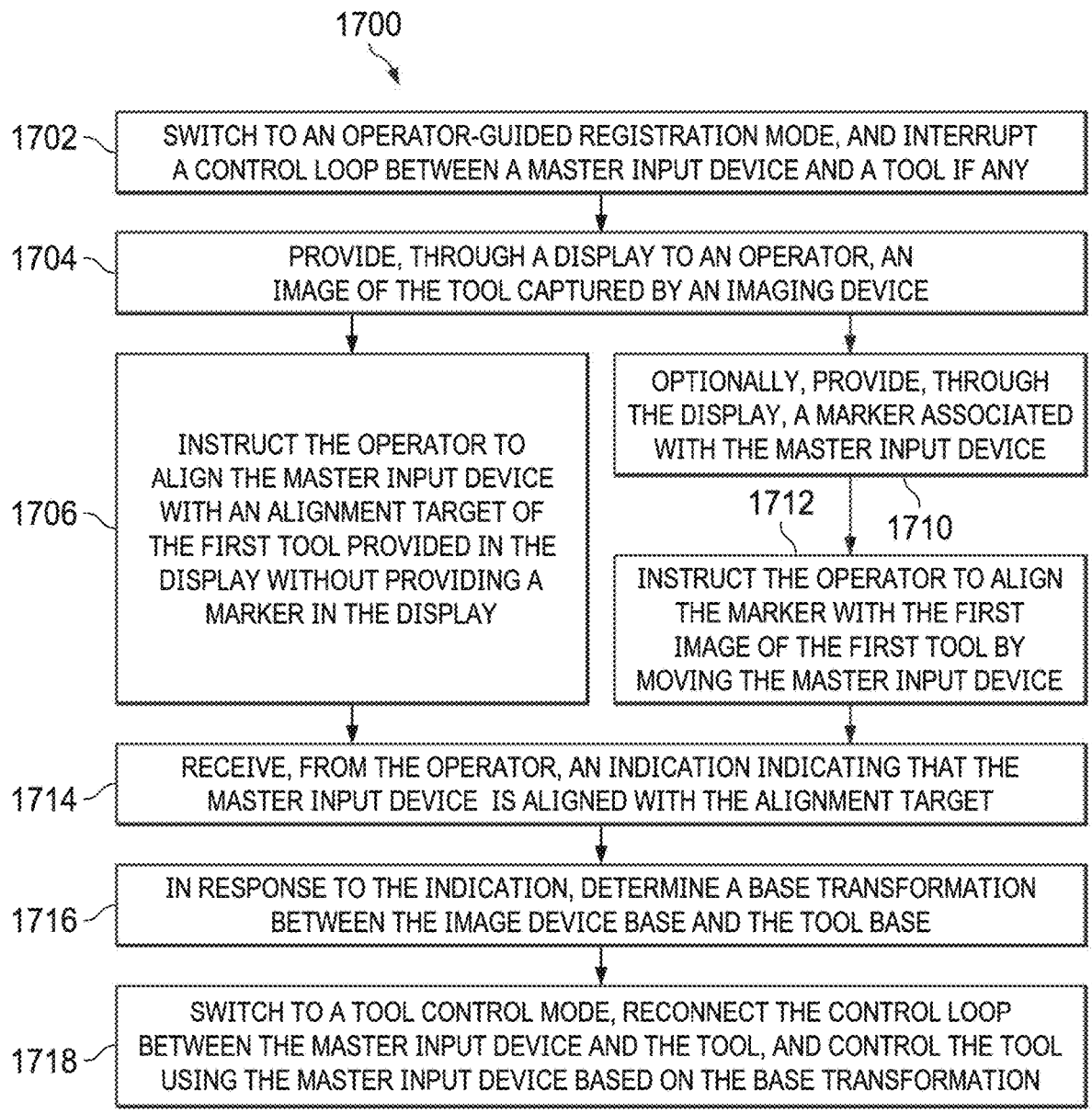
FIG. 17 is a flowchart providing a method for performing an operator-guided registration process for master-tool registration, in accordance with an embodiment of the present disclosure.

Referring to FIGS. 5 through 17, various systems and methods for performing an operator-guided registration process are described. As discussed above, to satisfy equation (2), the master control device needs to be aligned with the alignment target of the manipulator assembly 404 shown in a display of the operator's control console. In various embodiments, an alignment is considered to be achieved when an amount of misalignment is within a tolerance determined based on the needed motion accuracy. In an operator-guided registration process, an operator may perform an alignment step to move the master control device, and provide an indication to the control system after the operator determines that the master control device is aligned with the alignment target of the manipulator assembly 404 shown in a display of the operator's control console. In some embodiments, the control system instructs the operator to perform the alignment step without providing a marker on the display to assist the operator's alignment. Alternatively, as shown in FIGS. 5 through 16, a marker associated with the master control device may be provided on the display to assist the operator in the alignment step. FIG. 17 illustrates a flowchart of a method for performing an operator-guided registration process where an optional marker may be provided. Such an operator-guided registration process may use little or none imaging processing, which enables a time-efficient registration process. As such, the operator-guided registration process may be used both before and during an operation (e.g., a medical surgery operation) without causing long interruption to the operation.

In some embodiments, as illustrated in FIGS. 5 through 14, the operator-guided registration process may map a single rotational parameter for a base transformation between the camera base reference frame and the tool base reference frame. In those examples of FIGS. 5 through 14, the alignment target is a shaft 428 of the tool 14. Alternatively, in some embodiments as illustrated in FIGS. 15 and 16, the operator-guided registration process may map multiple parameters (translational and/or rotational parameters) for a base transformation between the camera base reference frame and the tool base reference frame. In those examples of FIGS. 15 and 16, the alignment target includes the shaft 428, the wrist 430, and the end effector 432 of the tool 14. It is noted that while in FIGS. 5 through 16 specific examples are used to describe the alignment target, the alignment target may include any portion of the manipulator assembly 404.

Referring to FIGS. 5, 6, 7, and 8, in some embodiments, a marker is shown on a display 500 (e.g., display 308) to assist an operator to move the master control device and determine that the master control device is aligned with the alignment target (e.g., the shaft 428). As discussed in detail below, depending on configuration of the operator-guided registration process (e.g., for mapping a single rotational parameter or mapping more than one translational and/or rotational parameters of the base transformation $^{b1}R_{b2}$, properties (e.g., shape, color, texture) of the alignment target), the marker may have various presentation properties including, for example, shape, color, size, translucency, surface patterns, text, any other presentation property, and/or a combination thereof. Such presentation properties of the maker may be used to indicate a direction (e.g., front or back) and an orientation (a roll angle representing a rotation around the X-axis). In an example, the marker (e.g., a cylinder) may not indicate a direction or an orientation. In another example, the marker may use various presentation properties, e.g., a particular shape (e.g., a cone), a color change, a pattern, a symbol, a text, and/or a combination thereof to indicate a direction and/or an orientation associated with the marker.

In the examples of FIGS. 5, 6, 7, and 8, the operator-guided registration process is configured to map a single rotational parameter (e.g., a bearing angle α around Z-axis) for a base transformation (e.g., $^{b1}R_{b2}$) between the camera base reference frame and the tool base reference frame. In those examples, a single-parameter marker associated with that single rotational parameter may be used to assist the operator S in the alignment step. The single-parameter marker may have a shape (e.g., a line, a cone, a cylinder) with an axis (e.g., an axis of symmetry) associated with that single parameter to be mapped. The operator S may align the single-parameter marker with an alignment target of the manipulator assembly 404 by moving the master control device, such that the axis of the single-parameter marker is aligned with the corresponding axis of the alignment target.

Figure 5:
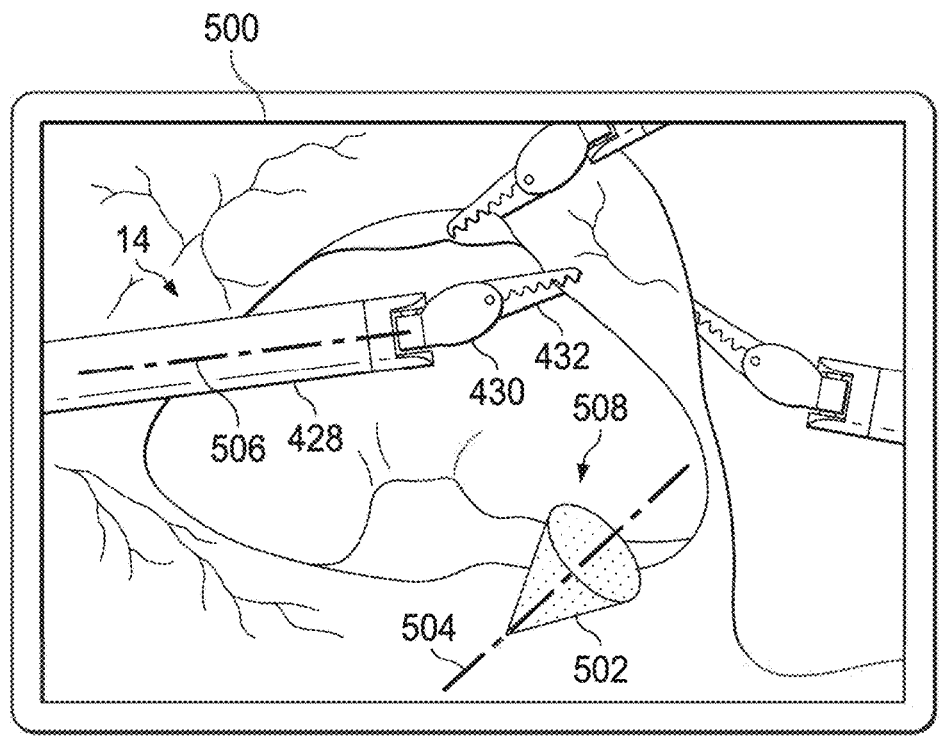
FIG. 5 illustrates an imaging view through a display of an operator's console before an operator performs an alignment step, in accordance with an embodiment of the present disclosure.
Figure 6:
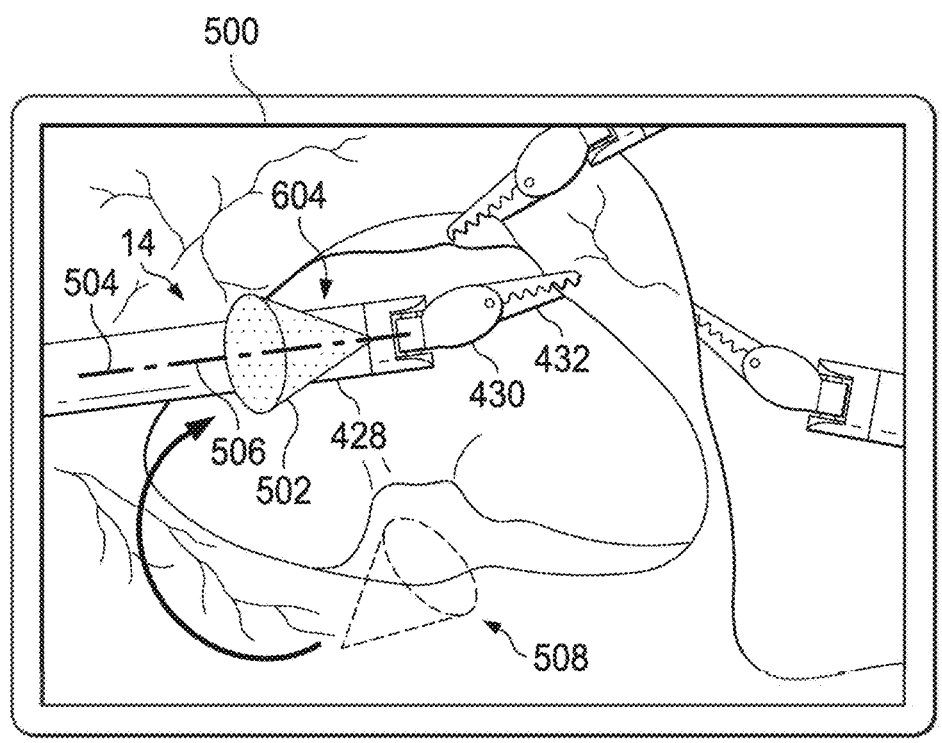
FIG. 6 illustrates an imaging view through a display of an operator's console after an operator performs an alignment step, in accordance with an embodiment of the present disclosure.
Figure 7:
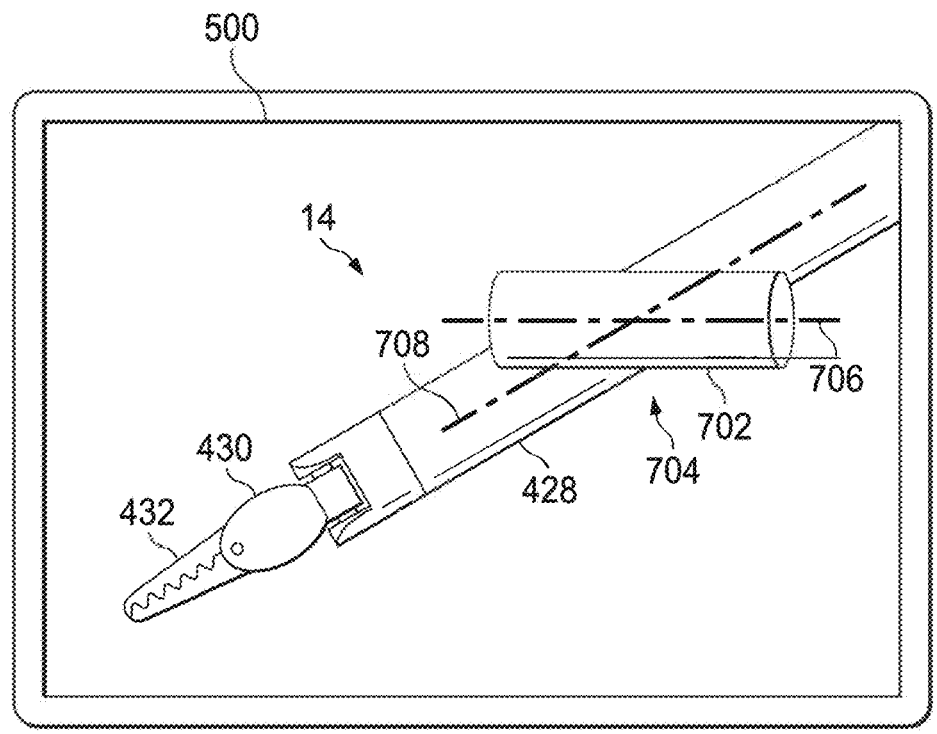
FIG. 7 illustrates an imaging view through a display of an operator's console before an operator performs an alignment step according to various embodiments of the present disclosure.
Figure 8:
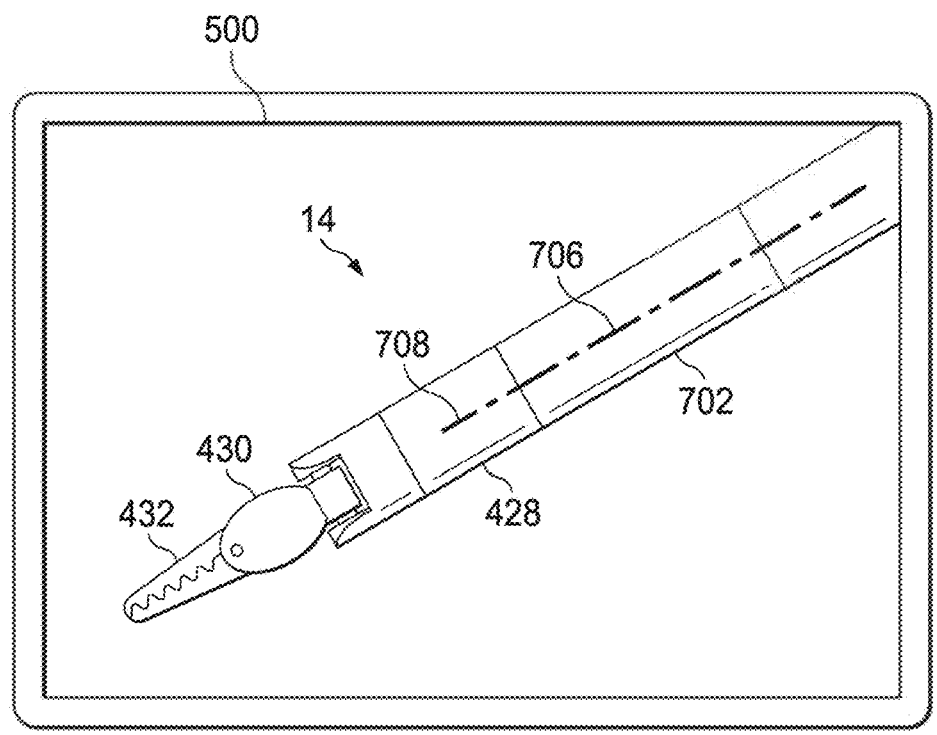
FIG. 8 illustrates an imaging view through a display of an operator's console after an operator performs an alignment step according to various embodiments of the present disclosure.

A marker with various shapes may be used. For example, the marker may have a one-dimensional shape (e.g., a straight line), a two-dimensional shape (e.g., a triangle, a square, a rectangle, a circle, an oval), and/or a three-dimensional shape (e.g., a cylinder, a pyramid, a prism, a cube, a rectangular prism). In various embodiments, a control system may determine a shape of the marker based on the required alignment accuracy. In the examples of FIGS. 5 and 6, the control system provides a marker 502 having a cone shape in the display. In the examples of FIGS. 7 and 8, the control system provides a marker having a shape (e.g., a cylinder) that is the same as that of the shaft 428, which may provide better alignment accuracy than the marker of FIGS. 5 and 6.

Referring to FIG. 5, illustrated therein is a display 500 (e.g., a display 308 of FIG. 3B) before the operator performs an alignment step of the operator-guided registration process. The display 500 shows a portion of the tool 14 that is in the field of view 416 of the imaging device 414. The portion of the tool 14 includes a portion of the shaft 428, the wrist 430, and the end effector 432. The display 500 also includes a cone marker 502 having a first position 508. The marker 502 has an axis 504 corresponding to the Z-axis of the master reference frame 202 of the master control device.

In various embodiments, the operator S may be instructed to move the master control device to change the position and/or orientation of the marker 502 in the display 500, such that the marker 502 is aligned with an alignment target (e.g., the shaft 428) in the display 500. In an example, the marker 502 is aligned with the shaft 428 in the display 500 after the axis 504 of the marker 502 is parallel to an axis 506 of symmetry of the shaft 428 in the display 500. The instruction may be provided to the operator S using a text message on the display 500 or an audio message provided through a speaker or a headphone worn by the operator S, such that the operator S may receive the instruction while viewing the display 500. In an example, the instruction may include an identification of the alignment target (e.g., a shaft 428, an end effector 432, an axis of symmetry of the shaft 428, an axis of symmetry of the end effector 432) to the operator S. In the particular example of FIG. 5, an instruction is provided to the operator S identifying the shaft 428 as the alignment target.

Referring to the example FIG. 6, illustrated therein is a display 500 after an operator S has performed an alignment step to move the marker 502 of FIG. 5 at the position 508 to position 604, so that the marker 502 of FIG. 6 has an orientation such that the marker 502 is aligned with the shaft 428 in the display. In the example of FIG. 6, the position of the marker 502 is moved so that its axis 504 is collinear with an axis 506 of symmetry of the shaft 428. In an alternative example, the marker 502 of FIG. 6 may remain at the same position as that of FIG. 5 but has a different orientation such that its axis 504 is parallel to the axis 506 of symmetry of the shaft 428. In an example, by aligning the axis 504 of the marker 502 and the corresponding axis 506 of the shaft 428 of the tool 14, alignment along the Z-axes of the master reference frame 202 and the shaft reference frame 436 is achieved.

In some embodiments, after the operator S determines that the marker 502 is aligned with the shaft 428 in the display 500 of FIG. 6, the operator S provides an indication using the master control device (e.g., using a hand grip, a button, a slider, a foot pedal, a voice recognition device, and the like) to the control system, indicating that the alignment step of the operator-guided registration process is completed. The control system may perform a registration step to compute the parameter to be mapped (e.g. bearing angle α around Z-axis) according to equations (10) and (11) or (12). The control system may then compute the base transformations $^{b1}R_{b2}$ using the bearing angle α according to equation (6) as discussed above.

Referring to FIGS. 7 and 8, in some embodiments, a marker may be presented on the display based on the alignment target, such that the operator may provide a more accurate alignment between the master control device and the alignment target. For example, the marker may have a shape, color, size, translucency, any other presentation property, and/or a combination thereof that are determined based on the alignment target.

In the example of FIG. 7, a display 500 includes a portion of the tool 14 in the field of view 416 of the imaging device 414 before an operator performs an alignment step. The portion of the tool 14 includes a shaft 428, a wrist 430 coupled to the distal end of the shaft 428, and an end effector 432 coupled to the wrist 430. In the example of FIG. 7, the shaft 428 has an axis 708 corresponding to the Z-axis of the shaft reference frame 436. The display 500 also includes a marker 702 at a position 704. The marker 702 has an axis 706 corresponding to the Z-axis of the master reference frame 202. In the example of FIG. 7, the marker 702 is a solid (i.e., not transparent/translucent) cylinder. In another example, the marker 702 is a semi-transparent or translucent image of the shaft 428. In yet another example, the marker 702 is a wire diagram image of the shaft 428. In the example of FIG. 7, the operator S may overlay the marker 702 with the shaft 428 by moving the master control device, which may help the operator S to achieve better alignment accuracy.

Referring to the example of FIG. 8, illustrated is the display 500 after the operator has performed an alignment step to move the marker 702 of FIG. 7. As shown in FIG. 8, by overlaying the marker 702 with the shaft 428, the operator may achieve better alignment accuracy.

Figure 11A:
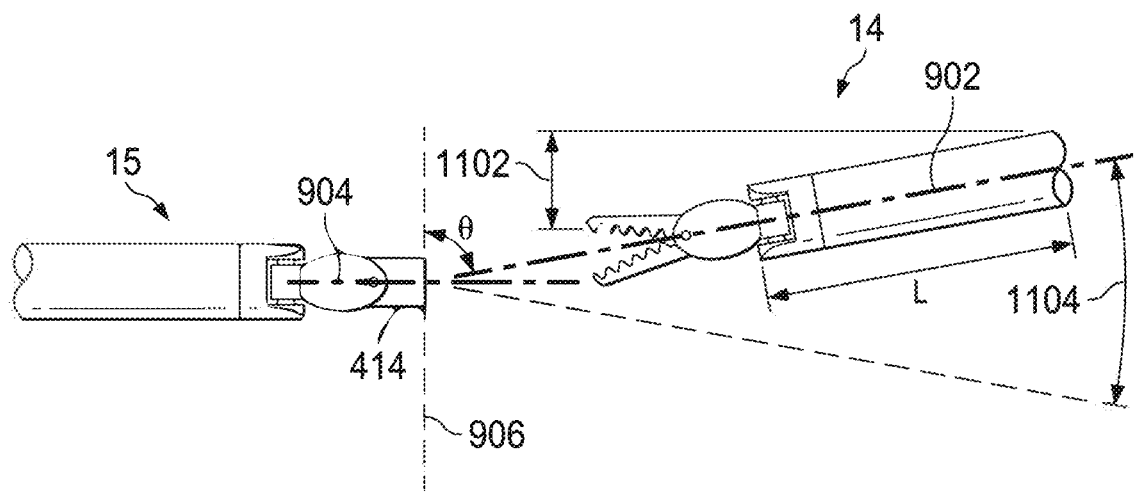
FIG. 11A is a schematic view illustrating a position of a tool relative to a viewing end of an imaging device, in accordance with an embodiment of the present disclosure.
Figure 11B:
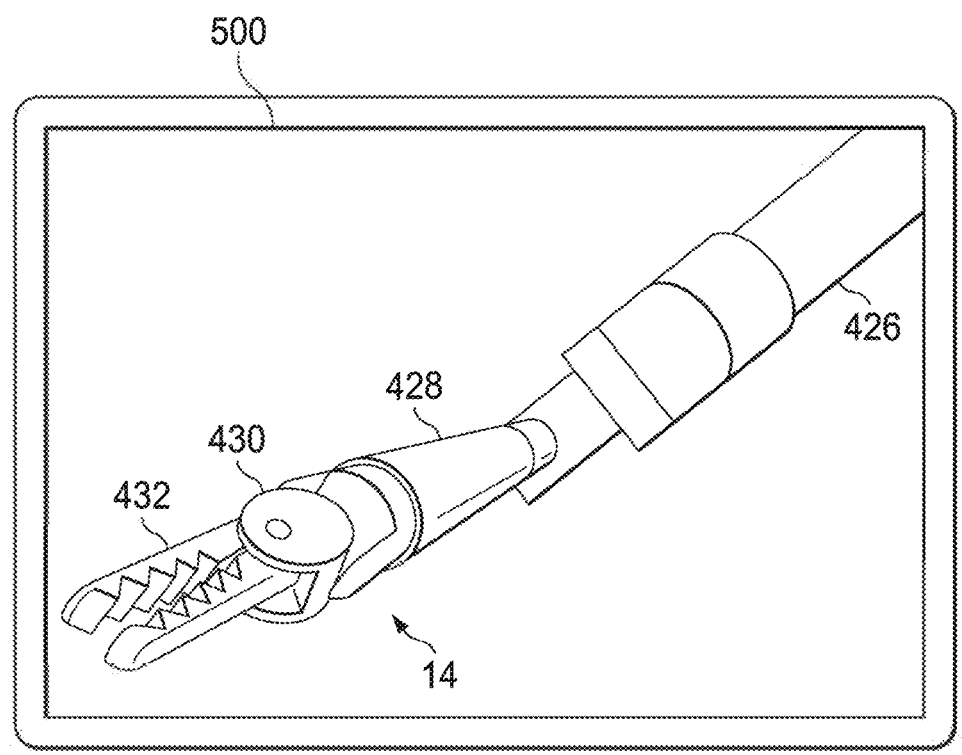
FIG. 11B illustrates an imaging view through a display of an operator's console including a field of view of the imaging device of FIG. 11A, in accordance with an embodiment of the present disclosure.
Figure 12:
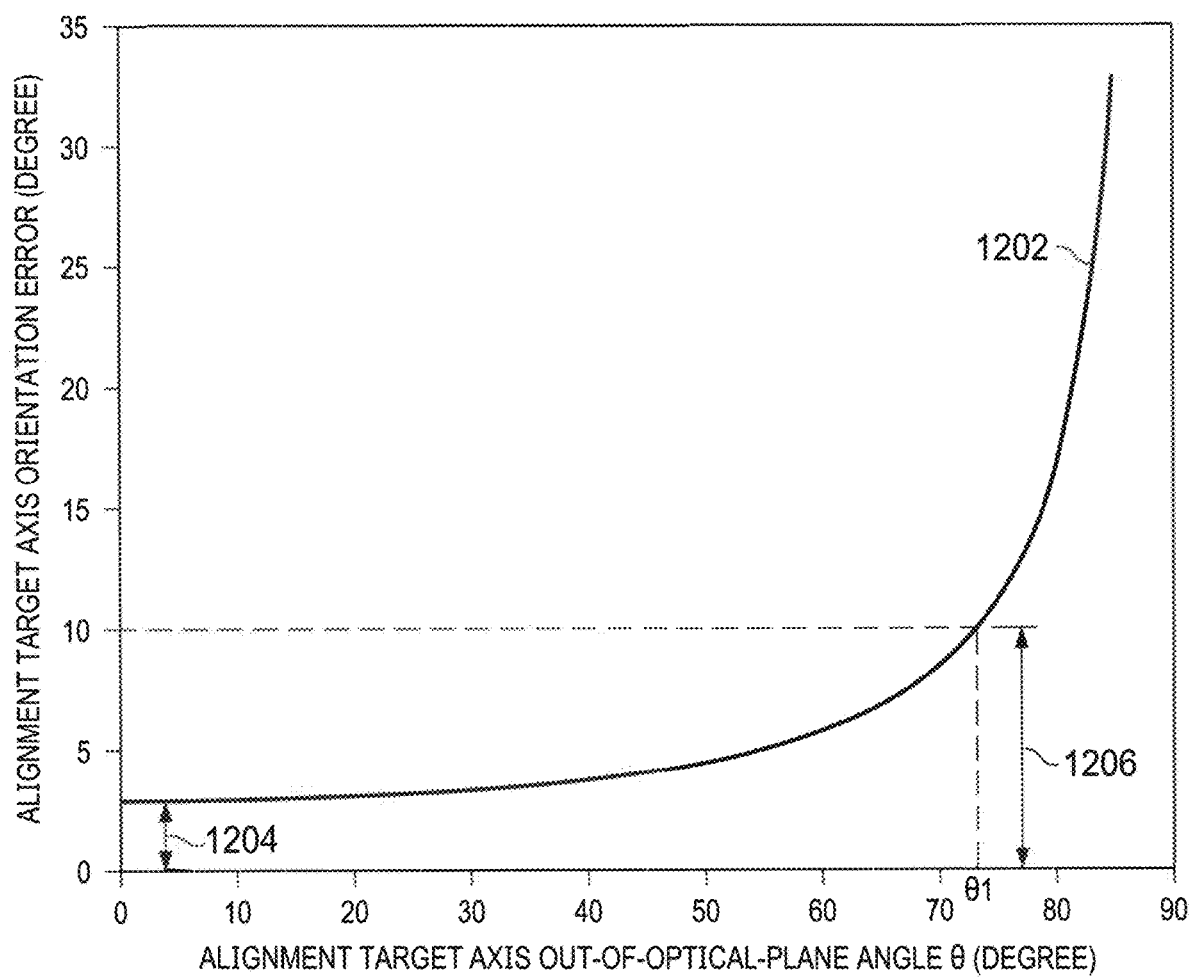
FIG. 12 illustrates a plot of the tool shaft axis orientation error with respect to the tool shaft axis out-of-optical plane angle, in accordance with an embodiment of the present disclosure.
Figure 13:
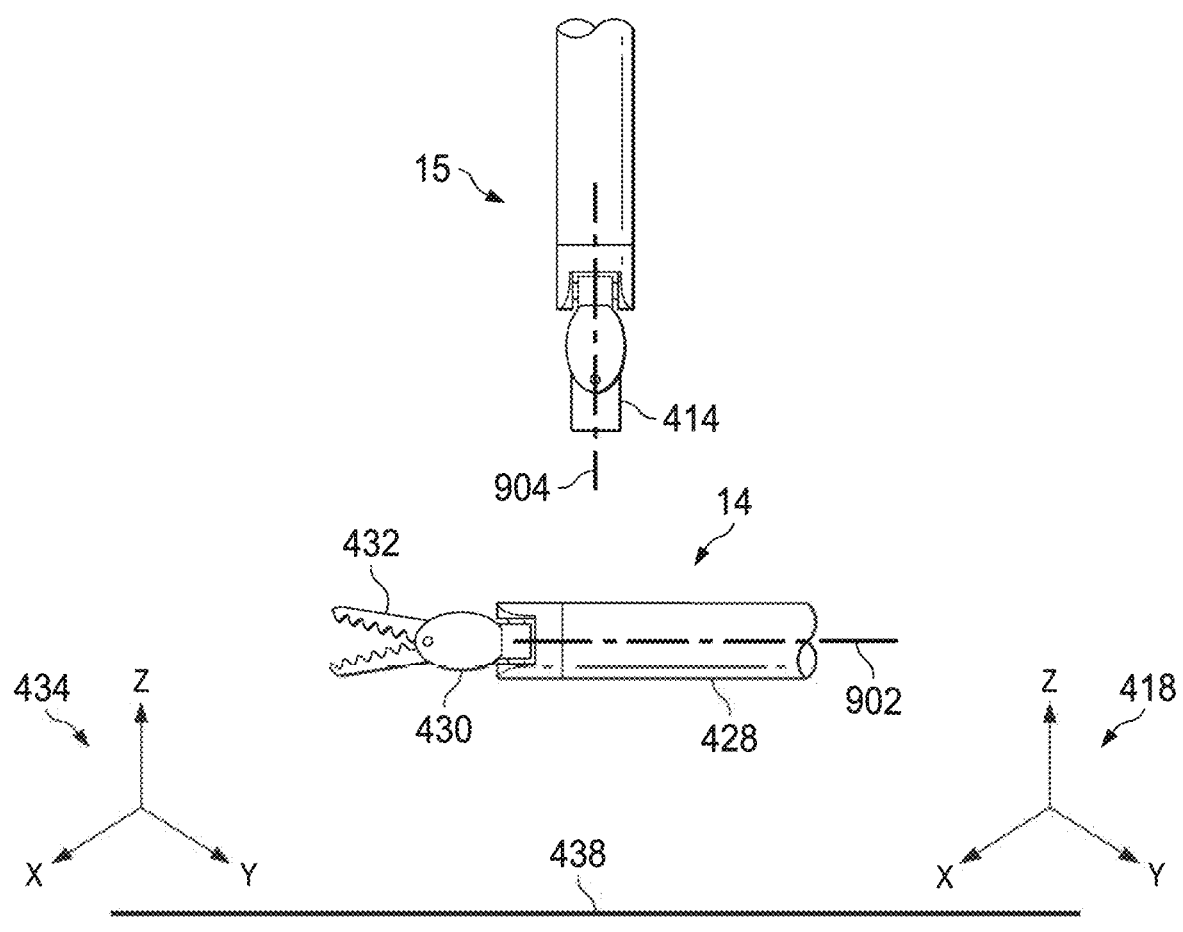
FIG. 13 illustrates a schematic view of a tool and an imaging device of a robotic medical system, in accordance with an embodiment of the present disclosure.
Figure 14:
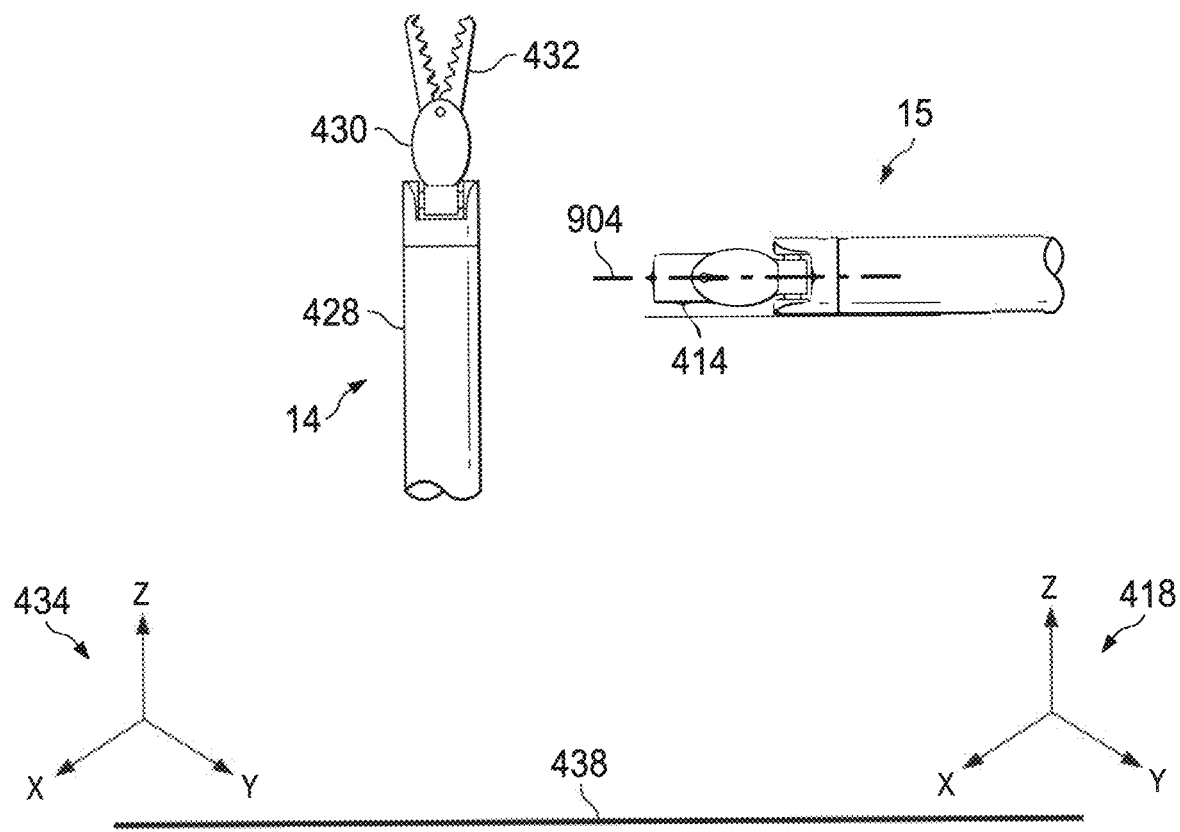
FIG. 14 illustrates a schematic view of a tool and an imaging device of a robotic medical system, in accordance with an embodiment of the present disclosure.

Referring to FIGS. 9A through 14, the operator-guided registration process may include two steps, an alignment step and a registration step. Each of the alignment step and registration step has its own best and worst cases regarding the positions and orientations of the tool 14 and/or the imaging device 414. FIGS. 9A through 12 illustrate the best and worst cases in alignment error sensitivity in the alignment step. FIGS. 13 and 14 illustrate the best and worst cases in the registration step. In some embodiments, prior to the alignment step and registration step of the operator-guided registration process, the manipulator assemblies 402 and/or 404 may be configured (e.g., manually by an operator or controlled using a master control device) such that they do not have configurations corresponding to the worst cases. In some embodiments, the control system may disable its operator-guided registration mode for performing the operator-guided registration process after it determines that the manipulator assemblies 402 and 404 have worst case configurations for the alignment and/or registration step, and enable the operator-guided registration mode after the manipulator assemblies 402 and 404 are moved out of the worst case configurations. In the examples of FIGS. 9A through 14, the alignment target is the shaft 428 of the tool 14. However, in other examples, the alignment target may be any portion of the manipulator assembly 404 controlling the tool 14.

Figure 9A:
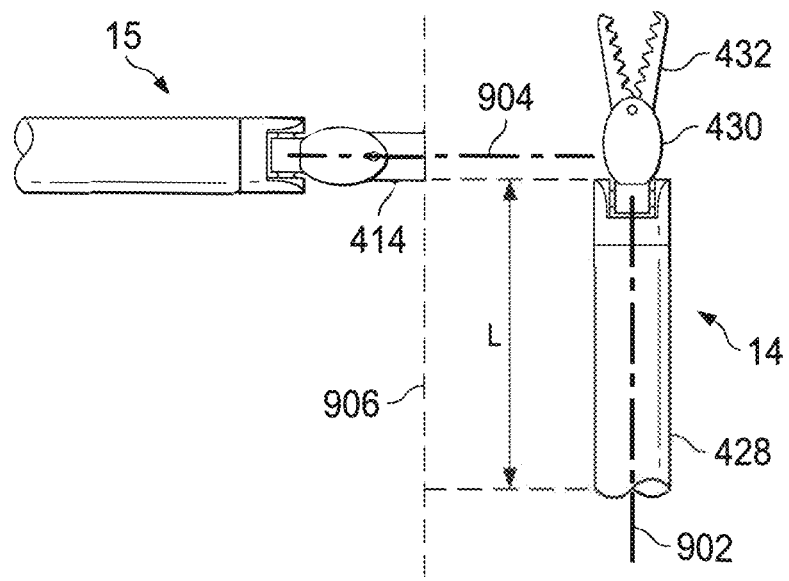
FIG. 9A is a schematic view illustrating a position of a tool relative to a viewing end of an imaging device, in accordance with an embodiment of the present disclosure.
Figure 9B:
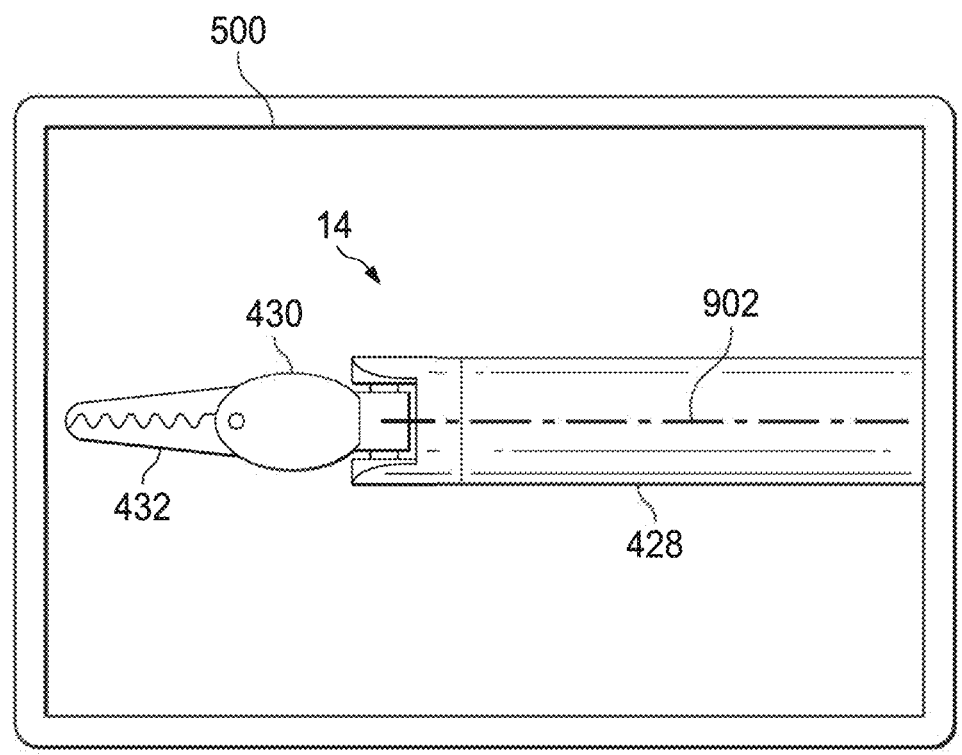
FIG. 9B illustrates an imaging view through a display of an operator's console including a field of view of the imaging device of FIG. 9A according to various embodiments of the present disclosure.

Referring to FIGS. 9A and 9B, illustrated therein is the best case configuration in the alignment step of the operator-guided registration process. FIG. 9A illustrates the relative positions and orientations of the shaft 428 and the imaging device 414. As shown in FIG. 9A, the shaft 428 of the tool 14 has an alignment target axis 902. The imaging tool 15 includes an imaging device 414 having an optical axis 904. The tool 14 and the imaging tool 15 are positioned such that the optical axis 904 is perpendicular to the alignment target axis 902. In other words, the shaft 428 of the tool 14 (the alignment target) lies entirely in a plane that is perpendicular to the optical axis 904 of the imaging device 414 and parallel to an optical plane 906 of the imaging device 414. In the example of FIG. 9A, the entire length L of the shaft 428 is projected on the optical plane 906.

FIG. 9B illustrates a display 500 including an image of the tool 14 captured by the imaging tool 15 of FIG. 9A. As shown in FIG. 9B, because the entire length L of the shaft 428 is projected on the optical plane 906, it is the easiest to orient a marker and align the marker to the alignment target axis 902 shown in the display 500. As such, such a configuration of relative positions of the tool 14 and the imaging tool 15 as shown in FIG. 9A is associated with the best alignment error sensitivity.

Figure 10A:
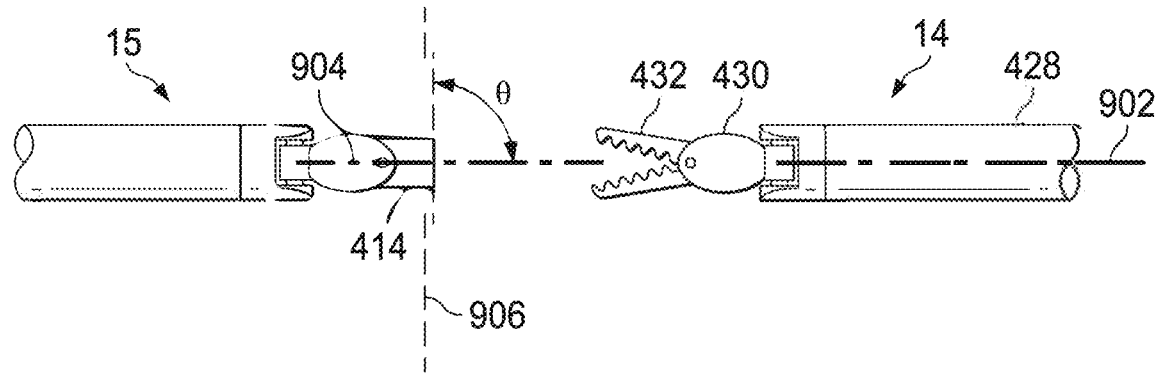
FIG. 10A is a schematic view illustrating a position of a tool relative to a viewing end of an imaging device, in accordance with an embodiment of the present disclosure.
Figure 10B:
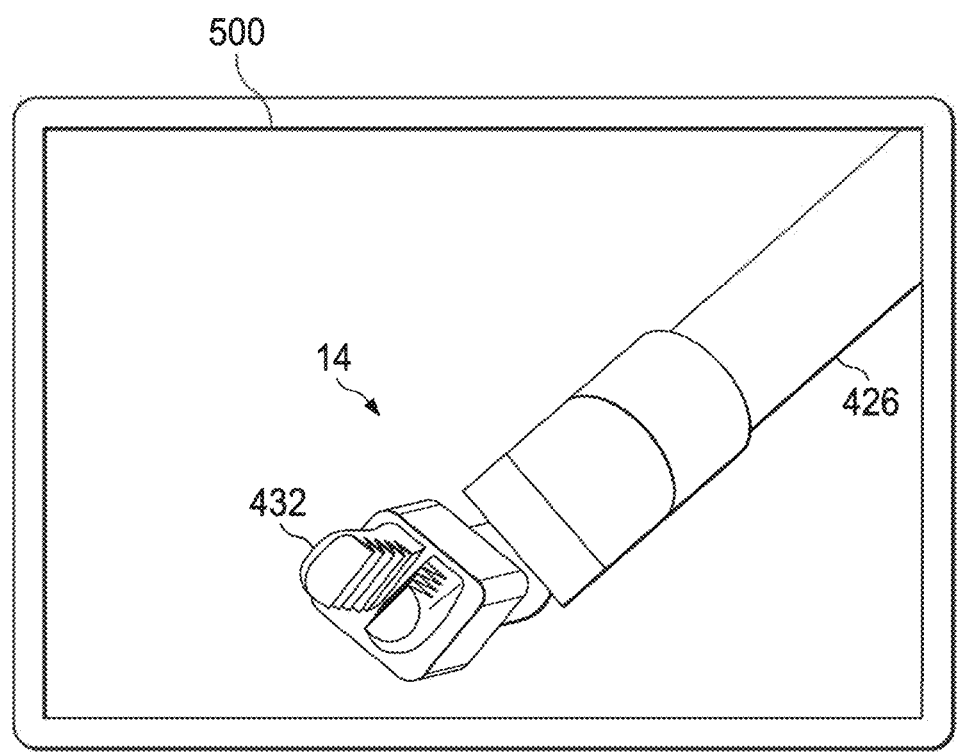
FIG. 10B illustrates an imaging view through a display of an operator's console including a field of view of the imaging device of FIG. 10A according to various embodiments of the present disclosure.

Referring to FIGS. 10A and 10B, illustrated therein is the worst case configuration in the alignment step of the operator-guided registration process. As shown in FIG. 10A, the shaft 428 of the tool 14 has an alignment target axis 902. The imaging tool 15 includes an imaging device 414 having an optical axis 904. The tool 14 and the imaging tool 15 are positioned such that the optical axis 904 is parallel to the alignment target axis 902. In other words, the axis of the shaft 428 of the tool 14 lies entirely in a plane parallel to the optical axis 904 of the imaging device 414. The alignment target axis 902 is perpendicular to the optical plane 906 of the imaging device 414, and has an out-of-plane angle θ of 90 degrees with regard to the optical plane 906. This is a singularity configuration in which the shaft 428 reduces to a circle in the field of view of the imaging device 414, and its alignment target axis 902 is projected as a point on the optical plane 906.

FIG. 10B illustrates a display 500 showing an image of the tool 14 captured by the imaging tool 15 of FIG. 10A. As shown in FIG. 10B, while a tip of the end effector 432 is visible on the display 500, the shaft 428 is not visible. In such a configuration, the operator S may not be able to orient a marker and align the marker to the shaft 428. As such, such a configuration of relative positions of the tool 14 and the imaging tool 15 as shown in FIG. 10A is associated with the worst alignment error sensitivity.

Referring to FIGS. 11A and 11B, even with an out-of-plane angle θ that is less than 90 degrees, it may be difficult for the operator S to align a marker with the shaft 428 as the out-of-plane angle θ gets closer to 90 degrees. As shown in the example of FIG. 11A, the shaft 428 and the imaging device 414 have relative positions and orientations such that an out-of-plane angle θ between an alignment target axis 902 of the shaft 428 and the optical plane 906 of the imaging device 414 is greater than zero but less than 90 degrees. The projected length 1102 of the shaft 428 on the optical plane 906 decreases as the output-of-plane angle θ increases from zero to 90 degrees. For example, the projected length 1102 may be computed using $L*\cos(\theta)$, where L is the length of the shaft 428. As the projected length 1102 decreases, it becomes more difficult for the operator S to align the marker to the shaft 428. For an identical translational error, a projected shaft having a shorter length results in a larger angular error. As such, the alignment error sensitivity decreases as the output-of-plane angle θ increases from zero to 90 degrees.

In an example, a threshold out-of-plane angle θ1 (e.g., 75 degrees) is provided indicating that at the threshold out-of-plane angle θ1, it becomes difficult for the operator S to align a marker with the shaft 428. An error region 1104 may be identified. In this example, a swivel angle cone may be identified as an error region 1104 where the out-of-plane angle θ is between the out-of-plane angle θ1 and 90 degrees. Such an error region may identify the bounds of the position/orientation of the shaft 428, where it is difficult for the operator S to align a marker with the shaft 428, or for the system to achieve sufficiently accurate registration given a particular operator-specified alignment. In an example, a control system may disable its operator-guided registration mode for performing the operator-guided registration mode after determining that the shaft 428 is in the error region 1104. In another example, the control system may provide an error region message to the operator notifying the operator of such worst case configuration. In yet another example, the control system may enable its operator-guided registration mode after determining that the shaft 428 is out of the error region 1104.

Referring to FIG. 12, a curve 1202 illustrates alignment target axis orientation errors with regard to the out-of-plane angle θ between the alignment target axis 902 and the optical plane 906 of the imaging device 414. As shown in the curve 1202, in a configuration (e.g., the configuration of FIGS. 9A and 9B) where the out-of-plane angle θ is zero, the alignment target axis orientation error has a value 1204 (e.g., about three degrees), which may be caused by a shaft position error (e.g., about 5%). As the out-of-plane angle θ increases from zero to 90 degrees, the alignment target axis alignment error increases. In a configuration (e.g., the configuration of FIGS. 10A and 10B) where the out-of-plane angle θ is 90 degrees, the alignment target axis alignment error is infinity.

In some embodiments, the control system includes a predetermined error threshold 1206 (e.g., 10 degrees) for the alignment target axis orientation error. As shown in FIG. 12, the predetermined alignment target axis orientation error threshold 1206 corresponds to an out-of-plane angle θ1 (e.g., 73 degrees). In such embodiments, bounds of an error region (e.g., a swivel angle cone-shaped error region 1104 of FIG. 11A) may be identified where the output-of-plane angle θ is between θ1 and 90 degrees. In a configuration where a shaft 428 is located within such an error region, it is difficult for the operator S to align the marker with the shaft 428 and is likely to result in an orientation error that is greater than the predetermined error threshold 1206. As such, prior to the operator-guided registration process, the imaging device 414 and the shaft 428 may be configured (e.g., manually by an operator or controlled using a master control device) such that the shaft 428 is not located in the error region. In an example, a control system may disable its operator-guided registration mode for performing the operator-guided registration mode after determining that the shaft 428 is in the error region. In another example, the control system may provide an error region message to the operator notifying the operator of such worst case configuration. In yet another example, the control system may enable its operator-guided registration mode after determining that the shaft 428 is out of the error region.

Referring to FIGS. 13 and 14, illustrated therein are the best and worst case configurations for the registration step of the operator-guided registration process, where the registration step uses alignment information provided by the alignment step of the operator-guided registration process. FIG. 13 illustrates the best case configuration for the registration step of the operator-guided registration process, which provides the most alignment information for registration. FIG. 14 illustrates the worst case configuration for the registration step of the operator-guided registration process, which provides the least alignment information for registration.

Referring to FIG. 13, illustrated therein is the best case configuration for the registration step of the operator-guided registration process, where an optical axis (e.g., optical axis 904) of the imaging device 414 is aligned with axes (e.g., Z-axes of the camera base frame 418 b1 and tool base frame 434 b2) associated with the content for registration (e.g., relative bearing angle α around the Z-axes of the camera base reference frame 418 and the tool base reference frame 434. In the example of FIG. 13, the camera base (e.g., base 406 of FIG. 4) for the imaging tool 15 and the tool base (e.g., base 422 of FIG. 4) are located on the same horizontal plane 438. As such, the Z-axes of the camera base reference frame 418 and the tool base reference frame 434 are vertical. The imaging device 414 of the imaging tool 15 has a position/orientation such that its optical axis 904 is parallel to the Z-axes of the camera base reference frame 418 and the tool base reference frame 434. The shaft 428 has a position/orientation such that its alignment target axis 902 is perpendicular to the optical axis 904. Such a configuration provides the maximum alignment information for registration (e.g., associated with the relative bearing angle α). After the alignment step is completed, an angle mismatch between the marker and the alignment target axis 902 (e.g., an angle between the Z-axes of the master control device frame and the shaft frame) is identical to the relative bearing angle α between camera base reference frame 418 and the tool base reference frame 434.

Referring to FIG. 14, illustrated therein is the worst case configuration for the registration step of the operator-guided registration process, where an optical axis (e.g., optical axis 904) of the imaging device 414 is perpendicular to the axes (e.g., Z-axes of camera base reference frame 418 and the tool base reference frame 434) associated with the content for registration (e.g., relative bearing angle α). In the example of FIG. 14, the camera base (e.g., base 406 of FIG. 4) for the imaging tool 15 and the tool base (e.g., base 422 of FIG. 4) are located on the same horizontal plane 438. As such, the Z-axes of the camera base reference frame 418 and the tool base reference frame 434 are vertical. The imaging device 414 of the imaging tool 15 has a position/orientation such that its optical axis 904 is perpendicular to the Z-axes of the camera base reference frame 418 and the tool base reference frame 434. Such a configuration provides no alignment information content for registration (e.g., relative bearing angle α between the bases 406 and 422 of FIG. 4). In such a configuration, even the best alignment of the marker and the shaft 428 during the alignment step may not provide any relevant information regarding the content for registration (e.g., relative bearing angle α between the bases 406 and 422). In other words, in this configuration, changing the position of the shaft 428 may not improve the relevant information content for registration.

As shown in FIGS. 13 and 14, relevant alignment information regarding the content for registration may reduce as the optical axis 904 of the imaging device 414 moves away from axes (e.g., Z-axes of the of camera base reference frame 418 and the tool base reference frame 434) associated with the content for registration (e.g., the bearing angle α). Such relevant alignment information reaches zero when the optical axis 904 of the imaging device 414 is perpendicular to the Z-axes of camera base reference frame 418 and the tool base reference frame 434. As such, in some embodiments, to avoid the worst case configuration in the registration step, prior to the operator-guided registration process, the imaging device 414 may be moved (e.g., manually by an operator) to a position/orientation based on the content for registration. In an example where the content for registration includes the bearing angle α associated with a Z-axis rotation of the bases, prior to the operator-guided registration process, the imaging device 414 is moved to a position where its optical axis is not perpendicular to the Z-axes of the bases. In another example where the content for registration includes additional translational parameters and rotational parameters associated with X, Y, and Z-axes of the camera base reference frame 418 and the tool base reference frame 434, prior to the operator-guided registration process, the imaging device 414 is moved to a position/orientation where its optical axis is not perpendicular to any of the associated X, Y, and Z-axes.

Referring to FIGS. 15 and 16, in some embodiments, the operator-guided registration process may map more than one parameter (translational and/or rotational parameters) of the base transformation $^{b1}R_{b2}$ between the camera base reference frame and the tool base reference frame. In some examples, the bases 406 and 422 may be on a tilted floor that has an angle with a horizontal plane and/or on a floor that is not even. In those examples, the operator-guided registration process may determine rotational parameters (e.g., a pitch angle R representing a rotation around the Y-axis and a roll angle γ representing a rotation around the X-axis) in addition to the bearing angle α representing a rotation around the Z-axis. In some examples, the operator-guided registration process may determine translational parameters (e.g., distances along the X, Y, and Z-axes) of the base transformation $^{b1}R_{b2}$, which may improve the master-tool transformation accuracy, thereby improving the operation intuitiveness in controlling the tool using the master control device.

Referring to the example of FIG. 15, illustrated is a display 500 includes an image of the tool 14 captured by the imaging tool 15 and a marker 1502 before an operator S performs an alignment step. The marker 1502 may be provided using a two-dimensional (2D) or a three-dimensional (3D) model of the tool 14, and thus may represent an actual solid model of the tool 14. The model of the tool 14 may be provided using, for example, computer aided design (CAD) data or other 2D or 3D solid modeling data representing the tool 14 (e.g., tool 14 of FIG. 4). In the example of FIG. 15, the marker 1502 is a virtual representation of the tool 14, and includes a virtual shaft 1504, a virtual wrist 1506, and a virtual end effector 1508. When the marker 1502 is in a virtual representation of a tool, the marker 1502 is also referred to as a virtual tool 1502 herein. The virtual tool 1502 and its position, orientation, and size as shown in the display 500 may be determined by the pose of the master control device and the alignment relationship between the master control device and the display 500. In an embodiment, the virtual tool 1502 is manipulatable at each joint (e.g., at the virtual wrist 1506) by the master control device, so that the pose of the tool 14 may be mimicked by the virtual tool 1502 by the operator S using the master control device in the alignment step. In the example of FIG. 15, the size of the virtual tool 1502 is smaller than the actual tool 14. The virtual tool 1502 may be represented in a number of different ways. In an example, the virtual tool 1502 is a semi-transparent or translucent image of the tool 14. In another example, the virtual tool 1502 is a wire diagram image of the tool 14. In yet another example, the virtual tool 1502 is an image that appears solid (i.e., not transparent/translucent), but such a solid virtual tool 1502 may make viewing of the actual tool 14 in the display 500 difficult.

Referring to the example of FIG. 16, illustrated is a display 500 after the operator S has performed the alignment step to move the master control device to overlay the virtual tool 1502 with the actual tool 14. The virtual tool 1502 has been moved based on the change in the alignment relationship between the master control device and the display. In other words, the position, orientation, and size of the virtual tool 1502 as shown in the display 500 of FIG. 16 correspond to the new pose of the master control device and the new alignment relationship between the master control device and the display after the operator S performs the alignment step.

In some embodiments, after the operator S determines that the virtual tool 1502 is aligned with (e.g., completely overlaying) the alignment target (e.g., the tool 14) in the display 500 of FIG. 16, the operator S provides an indication to the control system indicating that the alignment step of the operator-guided registration process is completed. In some embodiments, by overlaying the virtual tool 1502 completely with the tool 14, alignment information associated with all degrees of freedom is provided for the registration step. As such, the control system may compute one or more parameters (e.g., one or more of the six parameters in six total degrees of freedom in a three-dimensional space) according to equation (5). In an example, the transformation $^{b2}R_{target}$ in the equation (5) is a transformation between the tool base reference frame 434 to an end effector reference frame of the end effector 432.

While in the example of FIGS. 15 and 16, a marker 1502 that is a virtual representation of the tool 14 is used for multiple-parameter (e.g., three orientation parameters and the three translation parameters between the two base reference frames) mapping, the marker 1502 may use various visual indicators (e.g., markings, textures, colors, shapes, text) for such multiple-parameter mapping. In an example, the marker 1502 may include virsual indicators corresponding to particular features (e.g., flanges, indentations, protrusions) of the tool 14. In that example, an operator S may align the marker 1502 and the tool 14 in both positions and orientations by matching the marker 1502 with the image of the tool 14 in the display. As such, multiple-parameter mapping may be achieved.

FIG. 17 illustrates a method 1700 for performing an operator-guided registration process. The method 1700 is illustrated in FIG. 17 as a set of operations or processes 1702 through 1718. Not all of the illustrated processes 1702 through 1718 may be performed in all embodiments of method 1700. Additionally, one or more processes that are not expressly illustrated in FIG. 17 may be included before, after, in between, or as part of the processes 1702 through 1718. In some embodiments, one or more of the processes may be implemented, at least in part, in the form of executable code stored on non-transitory, tangible, machine-readable media that, when run by one or more processors (e.g., the processors of a control system such as control system 20), causes the one or more processors to perform one or more of the processes. As shown in the method 1700, little or no image processing is needed for such an operator-guided registration process. Therefore, the operator-guided registration process may take much less time than registration processes using computationally expensive image processing, and may be performed during a surgical operation. Furthermore, the operator-guided registration process may be performed without using additional sensors or other hardware in addition to the joint encoders in the manipulators, and may not suffer from sensor related restrictions such as line of sight, magnetic interference, etc.

The method 1700 begins at process 1702, where a control system of a robotic medical system is switched to an operator-guided registration mode. At process 1702, the control system may determine whether there is a control loop between a master control device and a tool, and interrupt that control loop if any. In other words, in the operator-guided registration mode, the tool is not controlled by the master control device. In an example, in the operator-guided registration mode, the control system may keep the tool and/or an imaging device stationary. In some embodiments, at process 1702, the control system may disable the operator-guided registration mode and/or provide a warning message to an operator after determining that an imaging device and a tool of the robotic medical system have configurations that correspond to the worst case configurations in alignment step and/or registration step as discussed above with reference to FIGS. 9A through 14.

The method 1700 may proceed to process 1704, where an image of a tool captured by an imaging device of the robotic medical system is provided to an operator through a display of an operator's console. In the example of FIG. 4, at process 1704, an image of a tool 14 is captured by an imaging device 414 of a robotic medical system. In the example of FIG. 5, an image including the field of view of the imaging device 414 is provided to an operator S through a display 500 of an operator's console. The displayed image may include portions of the tool 14 including, for example, shaft 428, wrist 430, and end effector 432.

In some embodiments, the method 1700 may then proceed to process 1706, where an operator S is instructed to align the master control device with an alignment target of the tool 14 provided in the display without the assistance of a marker in the display.

Alternatively, in some embodiments, the method 1700 may proceed to process 1710, where a marker is provided to the operator S through the display 500 to assist the operator S to perform an alignment step. In such embodiments, a control system may determine the type (e.g., single-parameter marker, multiple-parameter marker) of the marker based on the parameters to be determined by the operator-guided registration process.

In some embodiments, as shown in the examples of FIGS. 5, 6, 7, and 8, the operator-guided registration process is configured to determine a single parameter (e.g., a bearing angle α describing rotation around the Z-axis) of the base transformation $^{b1}R_{b2}$ from the camera base reference frame 418 to the tool base reference frame 434. In those embodiments, a single-parameter marker (e.g., marker 502 of FIG. 5, marker 702 of FIG. 7) associated with that single parameter (e.g., having an axis associated with the corresponding axis) may be used to assist the operator S to perform the alignment step. The single-parameter marker may have a shape (e.g., a line, a cone, a cylinder) with an axis (e.g., axis 504 of FIG. 5, axis 706 of FIG. 7) associated with the single parameter to be determined. In a subsequent process, the operator S may align the single-parameter marker with an alignment target of the tool by moving the master control device, such that the axis of the single-parameter marker is aligned with the corresponding alignment axis of the alignment target.

In some embodiments, as shown in the example of FIG. 15, the operator-guided registration process is configured to determine multiple parameters including rotational parameters (e.g., describing rotation about the X, Y, and Z-axes) and/or translational parameters (e.g., describing displacement along the X, Y, and Z-axes) associated with the base transformation $^{b1}R_{b2}$. In those embodiments, a multi-parameter marker (e.g., virtual tool 1502 of FIG. 15) associated with those multiple parameters may be used to assist the operator S in the alignment step. The multi-parameter marker may have a shape (e.g. a virtual representation of the tool 14) associated with those multiple parameters to be determined. In a subsequent process, the operator S may align the multi-parameter marker with the tool such that the multi-parameter marker and the tool completely overlay in the display by moving the master control device.

At process 1710, after determining the marker type, a marker of that determined marker type is shown in the display. The initial position and orientation of the marker on the display may be determined based on the alignment relationship between the master control device and the display and the pose of the master control device.

The method 1700 may then proceed to process 1712, where an operator S is instructed to align the marker with an alignment target of the tool provided in the display. In embodiments where a single parameter is to be determined, the operator S may be instructed to align the marker with an alignment target of the tool along a single axis. In the example of FIG. 5, the operator S may be instructed to control the position and orientation of the marker 502 using the master control device, such that the marker 502 is aligned with the shaft 428 of the tool 14 along axes 504 and 506. In the example of FIG. 7, the operator S may be instructed to control the position and orientation of marker 702 using the master control device, such that the marker 702 overlays the shaft 428 in the display 500. In the example of FIG. 15, the operator S may be instructed to control the position and orientation of the virtual tool 1502 using the master control device, such that the virtual tool 1502 and the tool 14 overlay in the display 500.

The method 1700 may then proceed to process 1714, where the control system receives, from the operator S, an alignment completion indication indicating that the master control device is aligned with the alignment target. The alignment completion indication may be provided by the operator S using the master control device (e.g., using a hand grip, a foot pedal, a voice recognition device, and the like). In the example FIG. 6, an operator S may provide such an alignment completion indication when the axis 504 of the marker 502 is parallel to or collinear with the shaft 428 of the tool 14 in the display 500. In the example of FIG. 8, the marker 702 has a shape (e.g., a cylinder) that is the same as that of the shaft 428. In that example, an operator S may provide such an alignment completion indication after the marker 702 overlays with the shaft 428 of the tool 14. In the example of FIG. 16, an operator S may provide such an alignment completion indication after the virtual tool 1502 (including its virtual shaft 1504, virtual wrist 1506, and virtual end effector 1508) overlays with the tool 14 (including its shaft 428, wrist 430, and end effector 432).

The method 1700 may then proceed to process 1716, where the control system determines the base transformation $^{b1}R_{b2}$ of the robotic medical system. In the examples of FIGS. 5, 6, 7, and 8, a single parameter (e.g., bearing angle α) may be computed according to equations (10), (11), and (12). In those examples, the base transformation $^{b1}R_{b2}$ may then be determined according to equation (6) using that single parameter. In the examples of FIGS. 15 and 16, multiple parameters (e.g., rotational parameters and translational parameters) may be computed according to equation (5). In those examples, the base transformation $^{b1}R_{b2}$ may then be determined according to equation (4) using those multiple parameters.

The method 1700 may then proceed to process 1718, where the control system switches to a tool control mode, and reconnects the control loop between the master control device and the tool. When operating in the tool control mode, the control system may control the movement of the tool relative to the camera frame in response to movement of a master control device associated with the tool. To effectively move the tool in the camera frame, the control system determines an alignment relationship between the camera reference frame and the end effector reference frame using the base transformation (e.g., $^{b1}R_{b2}$ determined at process 1716). For example, the control system may compute a transformation $^cR_{end\ effector}$ from the camera frame c to the end effector reference frame as follows:

$$^cR_{end\ effector} = {^cR_{b1}} * {^{b1}R_{b2}} * {^{b2}R_{end\ effector}}, \quad (13)$$

where $^cR_{b1}$ is a transformation from the camera reference frame 420 to the camera base reference frame 418, $^{b2}R_{end\ effector}$ is a transformation from the tool base reference frame 434 to the end effector reference frame. $^cR_{b1}$ and $^{b2}R_{end\ effector}$ are transformations that may be determined based on the forward and inverse kinematics of the manipulator assemblies 402 and 404 respectively, and $^{b1}R_{b2}$ is already determined previously at process 1718 by the operator-guided registration process.

In some embodiments, at process 1718, the control system may derive a master-tool transform in response to state variable signals provided by the imaging system, so that an image of the tool in a display appears substantially connected to the master control device. These state variables generally indicate the Cartesian position of the field of view of the imaging device, as supplied by the manipulator supporting the imaging device. The control system may derive the master-tool transform using the base transformation $^{b1}R_{b2}$ determined by the operator-guided registration process, such that the control system may properly control movement of the tool 14 relative to the camera frame in response to the movement of the master control device.

In various embodiments, the operator-guided registration process may be performed before or during an operation (e.g., a medical operation). In an medical example, the operator-guided registration process may be performed before the medical operation (e.g. during set-up) outside of the patient or inside the patient. In another example, the operator-guided registration process may be performed during the medical operation. In yet another example, the operator-guided registration process may be performed as a back-up and/or calibration-check registration method where another registration process (e.g., a registration process using sensors on the bases or a registration process using image processing) is the primary registration process. In yet another example, the operator-guided registration process may be used in a robotic system having manipulators on the same base to check and confirm registration of those manipulators with their respective tools.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor-readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read-only memory (ROM), a flash memory, an erasable programmable read-only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A robotic system comprising:
   an input device movable by an operator, wherein an operator reference frame is defined relative to the operator;
   a processing unit including one or more processors, the processing unit configured to:
   present, to the operator, a first image of a first tool captured by an imaging device;
   receive, from the operator, a first indication that a first axis of the input device is aligned with a corresponding axis of the first tool in the first image; and
   in response to the first indication, determine a first alignment relationship between the imaging device and the first tool based on a second alignment relationship between the operator reference frame and the input device.

2. The robotic system of claim 1, wherein the processing unit is further configured to:
   present, to the operator, a marker controlled by the input device based on the second alignment relationship to assist the operator to provide the first indication.

3. The robotic system of claim 2, wherein the marker includes a synthetic presentation of the first tool for the operator to overlay the marker with a shaft and an end effector of the first tool in the first image, or
   wherein the marker has an elongated shape for the operator to match the marker with a shaft of the first tool in the first image.

4. The robotic system of claim 1, further comprising:
   a first base having a first manipulator for coupling to the imaging device; and
   a second base physically separated from the first base having a second manipulator for coupling to the first tool;

wherein, to determine the first alignment relationship, the processing unit is configured to:
determine a base alignment relationship between the first base and the second base using the second alignment relationship between the operator reference frame and the input device; and
determine the first alignment relationship using the base alignment relationship.

5. The robotic system of claim 4, wherein the base alignment relationship is determined with a first rotational parameter.

6. The robotic system of claim 4, wherein the base alignment relationship is determined with a first translational parameter.

7. The robotic system of claim 4, wherein, to determine the first alignment relationship, the processing unit is configured to:
determine an imaging frame transformation from an imaging device reference frame of the imaging device to a first base frame associated with the first base;
determine a tool frame transformation from a second base frame associated with the second base to a tool reference frame associated with the first tool; and
determine the first alignment relationship using the imaging frame transformation, the base alignment relationship, and the tool frame transformation.

8. The robotic system of claim 7, wherein the imaging frame transformation is determined using one or more sensors positioned along a first kinematic chain extending from the first base to the imaging device, or wherein the tool frame transformation is determined using one or more sensors positioned along a second kinematic chain extending from the second base to the first tool.

9. The robotic system of claim 1, further comprising:
a first base having first and second manipulators,
wherein the first manipulator is configured to be coupled to the imaging device, and
wherein the second manipulator is configured to be coupled to the first tool.

10. A method comprising:
presenting, to an operator, a first image of a first tool captured by an imaging device;
receiving, from the operator, a first indication that a first axis of an input device movable by the operator is aligned with a corresponding axis of the first tool in the first image; and
in response to the first indication, determining a first alignment relationship between the imaging device and the first tool based on a second alignment relationship between an operator reference frame and the input device,
wherein the operator reference frame is defined relative to the operator.

11. The method of claim 10, further comprising:
presenting, to the operator, a marker controlled by the input device based on the second alignment relationship to assist the operator to provide the first indication.

12. The method of claim 11, wherein the marker includes a synthetic presentation of the first tool for the operator to overlay the marker with a shaft and an end effector of the first tool in the first image, or
wherein the marker has an elongated shape for the operator to match the marker with a shaft of the first tool in the first image.

13. The method of claim 10, wherein the determining the first alignment relationship comprises:

determining a base alignment relationship between a first base and a second base using the second alignment relationship between the operator reference frame and the input device,
wherein the first base has a first manipulator for coupling to the imaging device, and
wherein the second base is physically separated from the first base and has a second manipulator for coupling to the first tool.

14. The method of claim 13, wherein the base alignment relationship is determined with a first rotational parameter.

15. The method of claim 13, wherein the base alignment relationship is determined with a first translational parameter.

16. The method of claim 13, wherein the determining the first alignment relationship includes:
determining an imaging frame transformation from an imaging device reference frame of the imaging device to a first base frame associated with the first base;
determining a tool frame transformation from a second base frame associated with the second base to a tool reference frame associated with the first tool; and
determining the first alignment relationship using the imaging frame transformation, the base alignment relationship, and the tool frame transformation.

17. A non-transitory machine-readable medium comprising a plurality of machine-readable instructions which, when executed by one or more processors, are adapted to cause the one or more processors to perform a method comprising:
presenting, to an operator, a first image of a first tool captured by an imaging device;
receiving, from the operator, a first indication that a first axis of an input device movable by the operator is aligned with a corresponding axis of the first tool in the first image; and
in response to the first indication, determining a first alignment relationship between the imaging device and the first tool based on a second alignment relationship between an operator reference frame and the input device,
wherein the operator reference frame is defined relative to the operator.

18. The machine-readable medium of claim 17, wherein the method further comprises:
presenting, to the operator, a marker controlled by the input device based on the second alignment relationship to assist the operator to provide the first indication.

19. The machine-readable medium of claim 17, wherein the determining the first alignment relationship comprises:
determining a base alignment relationship between a first base and a second base using the second alignment relationship between the operator reference frame and the input device,
wherein the base alignment relationship is determined with a first rotational parameter,
wherein the first base has a first manipulator for coupling to the imaging device, and
wherein the second base is physically separated from the first base and has a second manipulator for coupling to the first tool.

20. The machine-readable medium of claim 17, wherein the determining the first alignment relationship comprises:
determining a base alignment relationship between a first base and a second base using the second alignment relationship between the operator reference frame and the input device, wherein the base alignment relationship is determined with a first translational parameter,
  wherein the first base has a first manipulator for coupling to the imaging device, and
  wherein the second base is physically separated from the first base and has a second manipulator for coupling to the first tool.

\* \* \* \* \*